United States Patent
Yamaya

(10) Patent No.: US 11,330,967 B2
(45) Date of Patent: May 17, 2022

(54) COVER AND ENDOSCOPE SYSTEM

(71) Applicant: OLYMPUS CORPORATION, Hachioji (JP)

(72) Inventor: Koji Yamaya, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 285 days.

(21) Appl. No.: 16/599,481

(22) Filed: Oct. 11, 2019

(65) Prior Publication Data
US 2020/0037861 A1 Feb. 6, 2020

Related U.S. Application Data

(63) Continuation of application No. PCT/JP2018/014434, filed on Apr. 4, 2018.

(30) Foreign Application Priority Data

Apr. 11, 2017 (JP) .............................. JP2017-078317

(51) Int. Cl.
*A61B 1/00* (2006.01)

(52) U.S. Cl.
CPC ...... *A61B 1/00135* (2013.01); *A61B 1/00089* (2013.01); *A61B 1/00091* (2013.01);
(Continued)

(58) Field of Classification Search
CPC ............ A61B 1/00089; A61B 1/00098; A61B 1/00101
See application file for complete search history.

(56) References Cited

U.S. PATENT DOCUMENTS 4,881,810 A  11/1989 Hasegawa
5,662,588 A *  9/1997 Iida ................... A61B 1/00091
                                                      600/121
(Continued)

FOREIGN PATENT DOCUMENTS

GN  204562074 U  8/2015
JP  S52141892 U  10/1977
(Continued)

OTHER PUBLICATIONS

Dec. 11, 2018 Office Action issued in Japanese Patent Application No. 2018-559896.
(Continued)

*Primary Examiner* — Matthew J Kasztejna
(74) *Attorney, Agent, or Firm* — Oliff PLC

(57) ABSTRACT

A cover includes a cover body and a covering portion. The cover body can include an opening edge exposing a part of a distal structure portion, an annular portion surrounding a periphery of the distal structure portion, a proximal edge, a dividing portion provided in the annular portion in a manner to define a slit that is continuous with the opening edge portion and the proximal edge portion, and an overlapping portion. The dividing portion includes a first cylindrical wall portion, and a second cylindrical wall portion. The first cylindrical wall portion and the second cylindrical wall portion overlap at least partly in the overlapping portion. The covering portion is configured to cover a part, where at least the dividing portion is provided.

17 Claims, 15 Drawing Sheets

(52) U.S. Cl.
CPC ...... *A61B 1/00098* (2013.01); *A61B 1/00101* (2013.01); *A61B 1/00137* (2013.01)

(56) References Cited

U.S. PATENT DOCUMENTS

| | | | | |
|---|---|---|---|---|
| 5,674,181 | A * | 10/1997 | Iida | A61B 1/0008 600/127 |
| 5,730,701 | A * | 3/1998 | Furukawa | A61B 1/0008 600/121 |
| 8,038,604 | B2 * | 10/2011 | Hamazaki | A61B 1/00142 600/127 |
| 8,747,304 | B2 * | 6/2014 | Zeiner | A61B 1/018 600/127 |
| 9,949,619 | B2 * | 4/2018 | Iizuka | A61B 1/00142 |
| 11,116,385 | B2 * | 9/2021 | Hosogoe | A61B 1/00137 |
| 2001/0016679 | A1 | 8/2001 | Futatsugi et al. | |
| 2003/0009085 | A1 * | 1/2003 | Arai | A61B 1/00089 600/127 |
| 2018/0140171 | A1 | 5/2018 | Yamaya | |

FOREIGN PATENT DOCUMENTS

| | | |
|---|---|---|
| JP | S63-234935 A | 9/1988 |
| JP | H5-184534 A | 7/1993 |
| JP | H09-75295 A | 3/1997 |
| JP | 2001-212075 A | 8/2001 |
| JP | 2003-102668 A | 4/2003 |
| WO | 2017/006705 A1 | 1/2017 |

OTHER PUBLICATIONS

Oct. 15, 2019 Translation of International Preliminary Report on Patentability issued in International Patent Application No. PCT/JP2018/014434.

Jul. 3, 2018 International Search Report issued in International Patent Application No. PCT/JP2018/014434.

May 8, 2021 Office Action issued in Chinese Patent Application No. 201880022172.5.

* cited by examiner

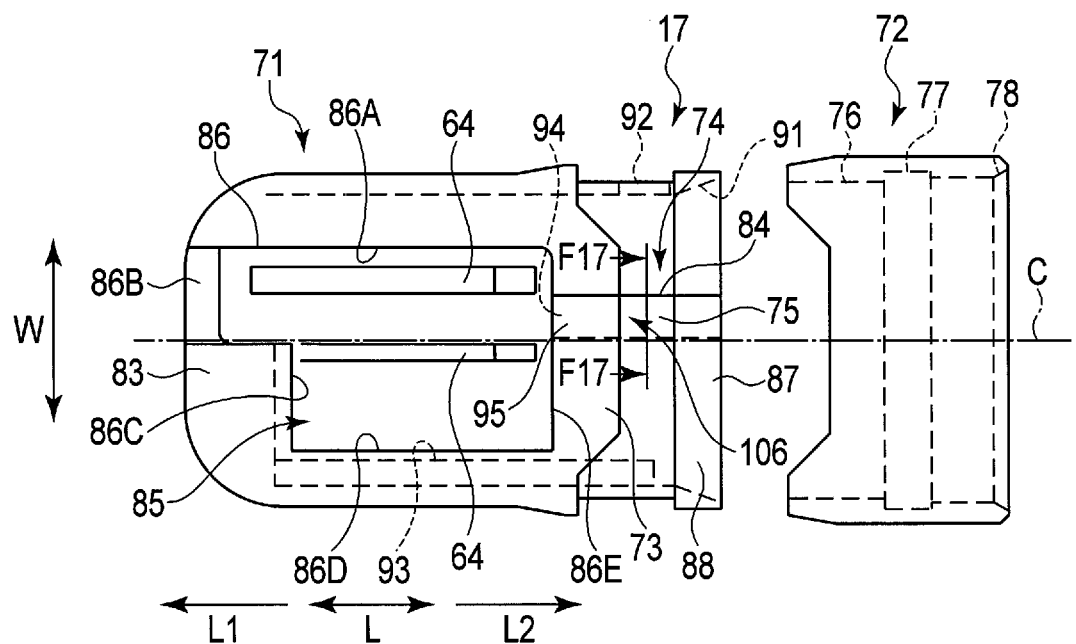
F I G. 16

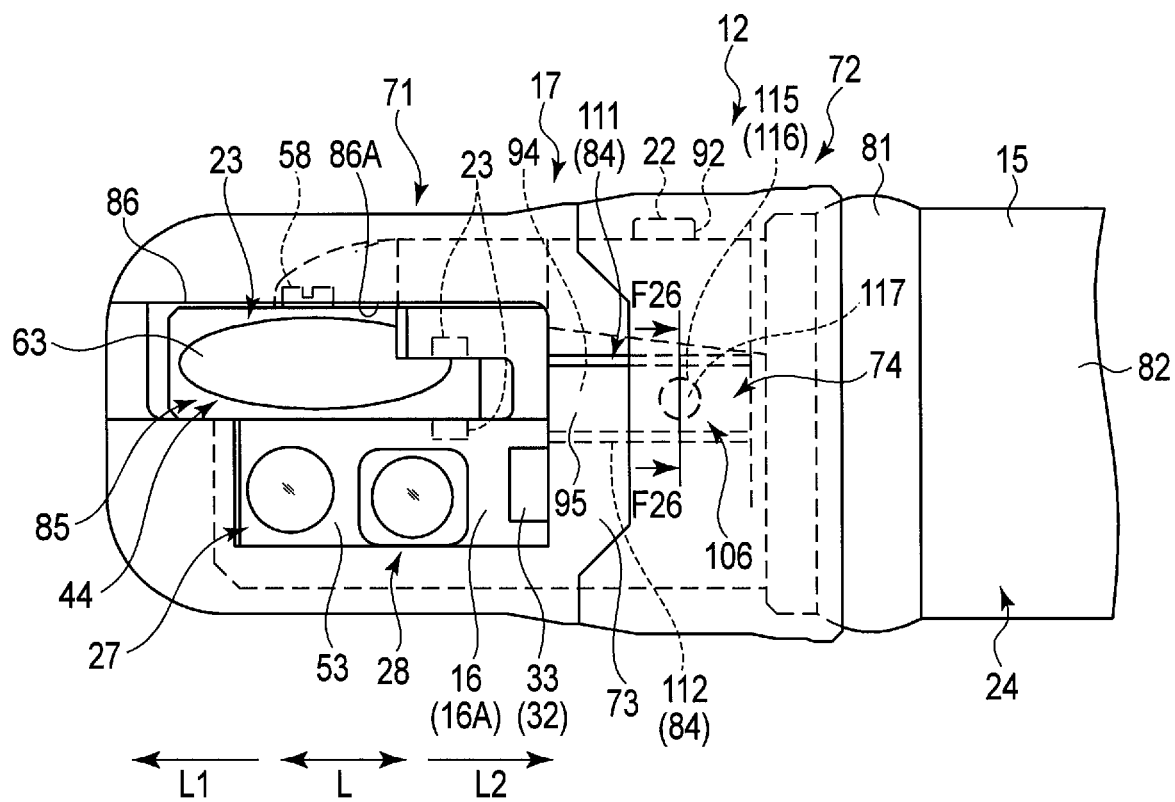
F I G. 25
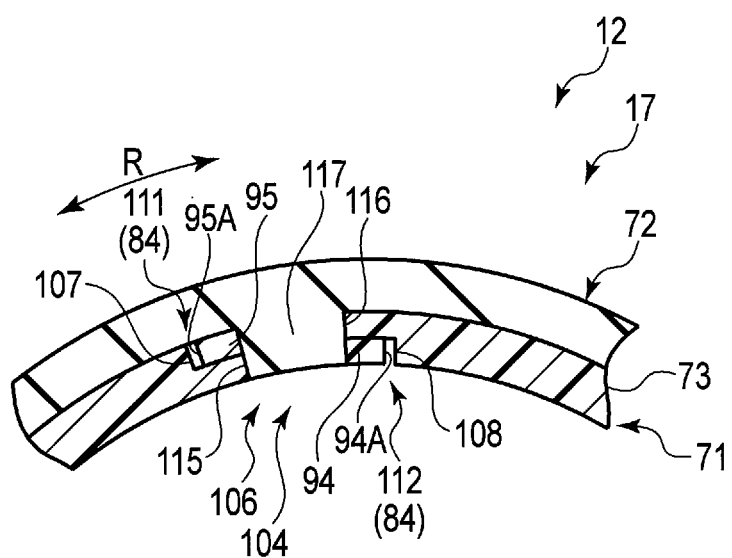
F I G. 26

COVER AND ENDOSCOPE SYSTEM

CROSS-REFERENCE TO RELATED APPLICATIONS

This application is a Continuation Application of PCT Application No. PCT/JP2018/014434, filed Apr. 4, 2018 and based upon and claiming the benefit of priority from prior Japanese Patent Application No. 2017-078317, filed Apr. 11, 2017, the entire contents of all of which are incorporated herein by reference.

BACKGROUND

For example, Jpn. Pat. Appln. KOKAI Publication No. 2003-102668 discloses an endoscope which is inserted into the body and is used for observation of the inside of the body. Usually, in the endoscope, a cap is provided at a distal end of an insertion section, and the surrounding of a distal structure portion, which is provided at the distal end of the insertion section, is covered by the cap. By this structure, a mucous membrane in a body cavity of a patient is protected.

BRIEF SUMMARY

A cover attached to a distal structure portion of an insertion section of an endoscope can include: a cover body including: an opening edge portion which defines a surrounding of an opening that exposes a part of the distal structure portion, an annular portion which surrounds a periphery of the distal structure portion, a proximal edge portion which is provided on the annular portion and is located at a distal end in a longitudinal direction of the insertion section, a dividing portion which is provided in the annular portion in a manner to define a slit that is continuous with the opening edge portion and the proximal edge portion, the dividing portion including: a first cylindrical wall portion that is a part of the annular portion including a first edge, and a second cylindrical wall portion that is a part of the annular portion including a second edge, and an overlapping portion in which the first cylindrical wall portion and the second cylindrical wall portion overlap at least partly; and a covering portion configured to cover a part of the annular portion, where at least the dividing portion is provided.

Advantage of the invention will be set in the description of the follow, and in part will be obvious from the description or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constituent a part of the specification, illustrate exemplary embodiments and together with the general description given above and the detailed description of the embodiments given below, serve to explain the principles.

FIG. 16 is an exploded plan view illustrating a cover body of an endoscope system according to an exemplary embodiment.

FIG. 25 is a plan view illustrating a distal structure portion of an endoscope system of an exemplary embodiment, and a cover which covers the distal structure portion.

FIG. 26 is a cross-sectional view of the cover illustrated in FIG. 25, FIG. 26 being taken along line F26-F26 in FIG. 25.

DETAILED DESCRIPTION

Figure 1:
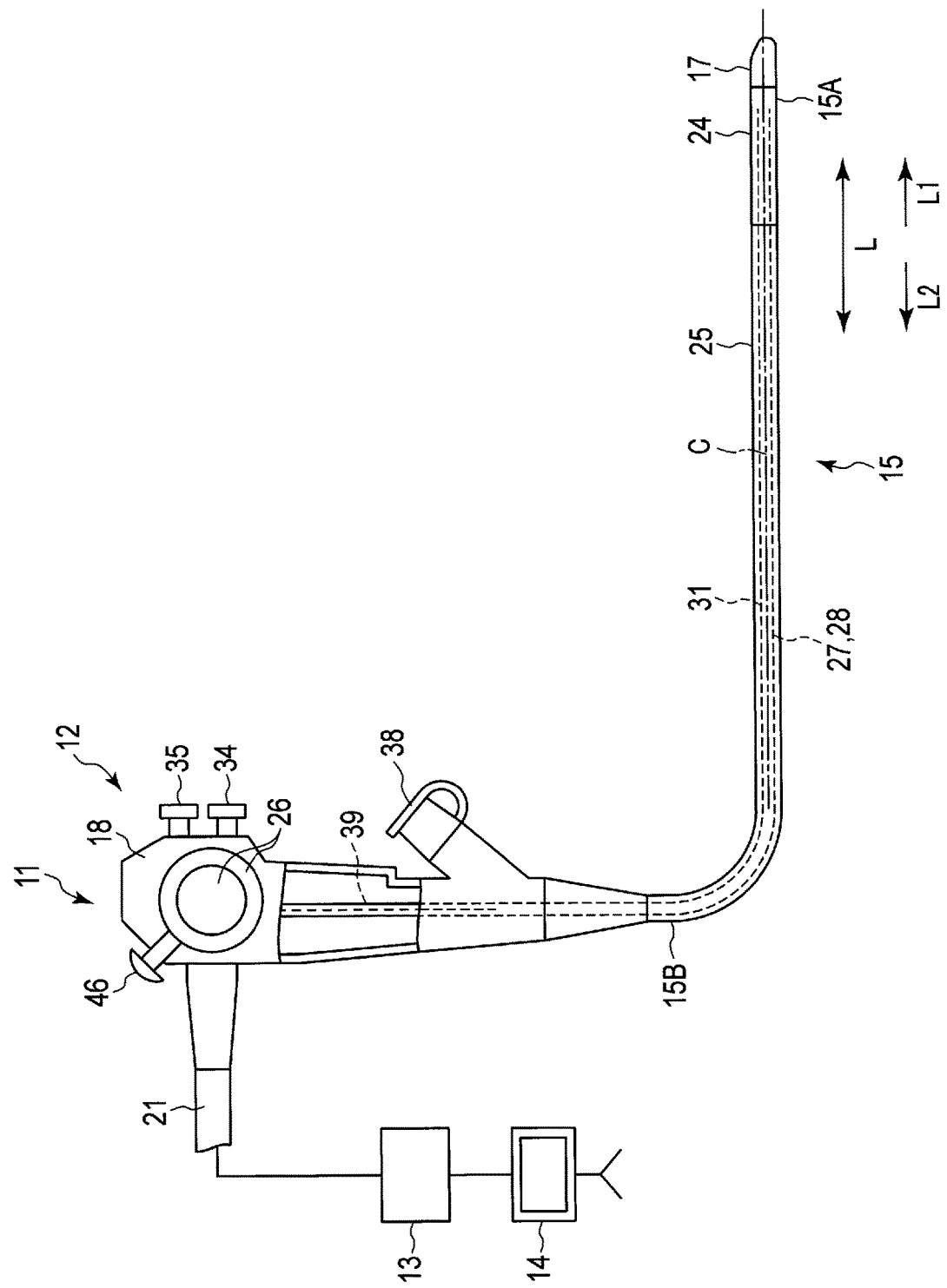
FIG. 1 is a schematic view illustrating an endoscope system according to an exemplary embodiment.

As illustrated in FIG. 1, an endoscope system 11 can include an endoscope 12; an endoscope controller 13 (image processing unit) which performs image processing, based on a subject image captured by the endoscope 12; and a monitor 14 which displays video that is generated by the image processing in the endoscope controller 13.

Figure 2:
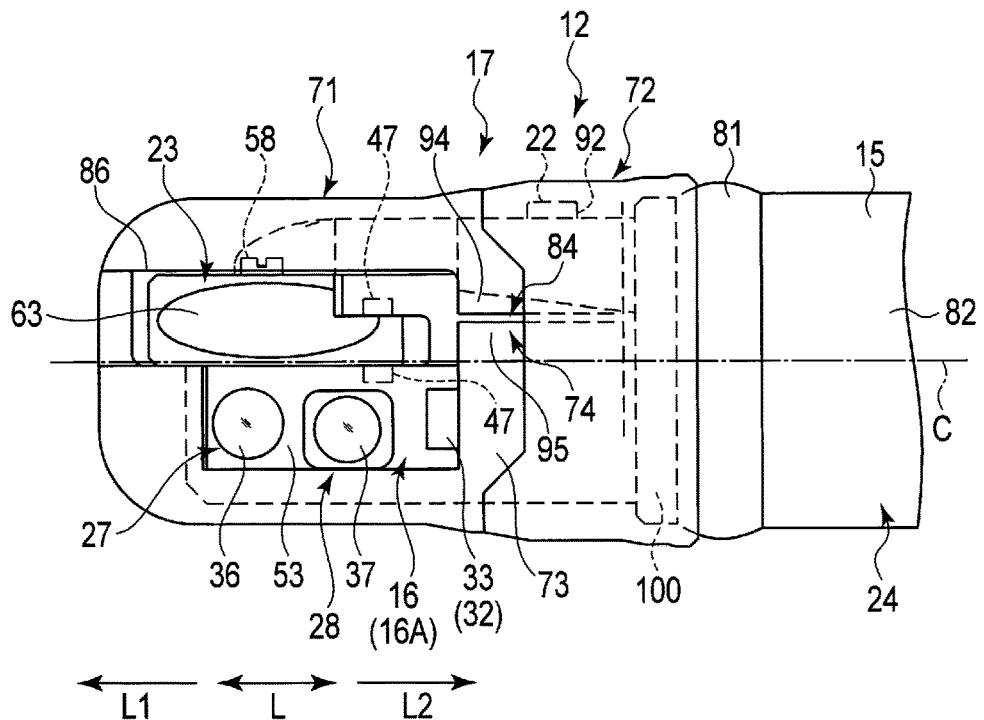
FIG. 2 is a plan view illustrating a distal structure portion of the endoscope system illustrated in FIG. 1, and a cover which covers the distal structure portion.

As illustrated in FIG. 1 and FIG. 2, the endoscope 12 (insertion device) includes an insertion section 15 which is inserted into a tract such as a lumen cavity of a subject along a longitudinal direction L; a rigid distal structure portion 16 provided on a distal side of the insertion section 15; a cover 17 (exterior member, jacket) which is attached to the distal structure portion 16; an operation section 18 which is provided at a proximal end of the insertion section 15 and is grasped by a user; and a universal cord 21 extending from the operation section 18. Although details will be described later, the cover 17 is formed as a disposable type. The cover 17 is easily attachable to the distal structure portion 16 while the shape thereof is being maintained. However, the cover 17 is formed not to be easily detachable from the distal structure portion 16, for example, by an engaging pin 22 (to be described later) or the like.

As illustrated in FIG. 1, the insertion section 15 defines the longitudinal direction L by a distal end 15A and a proximal end 15B thereof. The longitudinal direction L is a direction along a center axis C of the insertion section 15. As illustrated in FIG. 1 and FIG. 2, the insertion section 15 includes a pivot base 23, the distal structure portion 16, a bending portion 24 and a tube portion 25 in the named order from the distal end 15A toward the proximal end 15B thereof. The tube portion 25 may be a flexible one which is a so-called flexible endoscope, or may be a so-called rigid endoscope which keeps a straight state and has resistance to bending. The bending portion 24 can be bent in a plurality of directions, for example, in two directions or four directions, by a knob 26 of the operation section 18 by a publicly known mechanism. Note that, in the embodiments to be described below, the description will be given by defining a distal direction of the longitudinal direction L as L1, and by defining a proximal direction opposite to the distal direction of the longitudinal direction L as L2.

Figure 3:
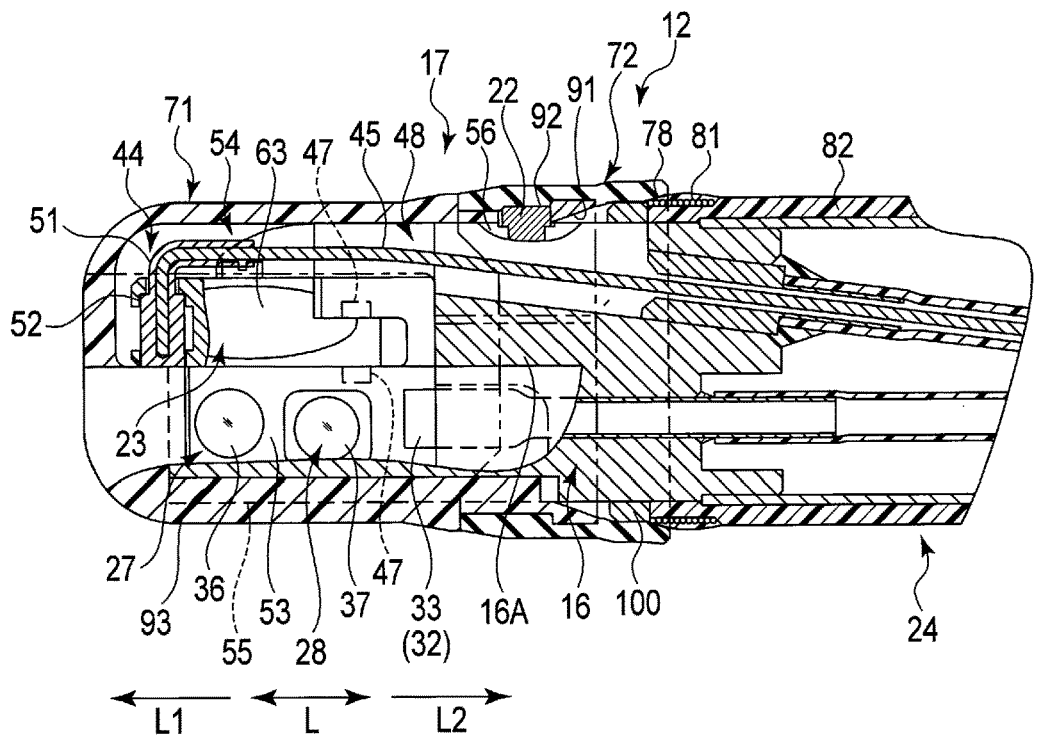
FIG. 3 is a cross-sectional view illustrating an insertion section of an endoscope, the distal structure portion and the cover, which are illustrated in FIG. 2, FIG. 3 being taken by a plane along a central axis C.

As illustrated in FIG. 1 to FIG. 3, the endoscope 12 includes an illumination optical system 27, an observation optical system 28 and a treatment instrument insertion channel 31. Besides, the endoscope 12 includes an air/water supply mechanism 32 and a suction mechanism (not shown). The air/water supply mechanism 32 includes a nozzle 33 (to be described) at a distal end thereof, and is operated by a first button 34 of the operation section 18. The suction mechanism communicates with the treatment instrument insertion channel 31, and is operated by a second button 35 of the operation section 18.

The illumination optical system 27 and observation optical system 28 are inserted through the distal structure portion 16, bending portion 24 and tube portion 25 of the insertion section 15 of the endoscope 12, the operation section 18, and the universal cord 21. As illustrated in FIG. 2, the illumination optical system 27 includes an illumination window 36 in the distal structure portion 16. The observation optical system 28 includes an observation window 37 in the distal structure portion 16.

Figure 12:
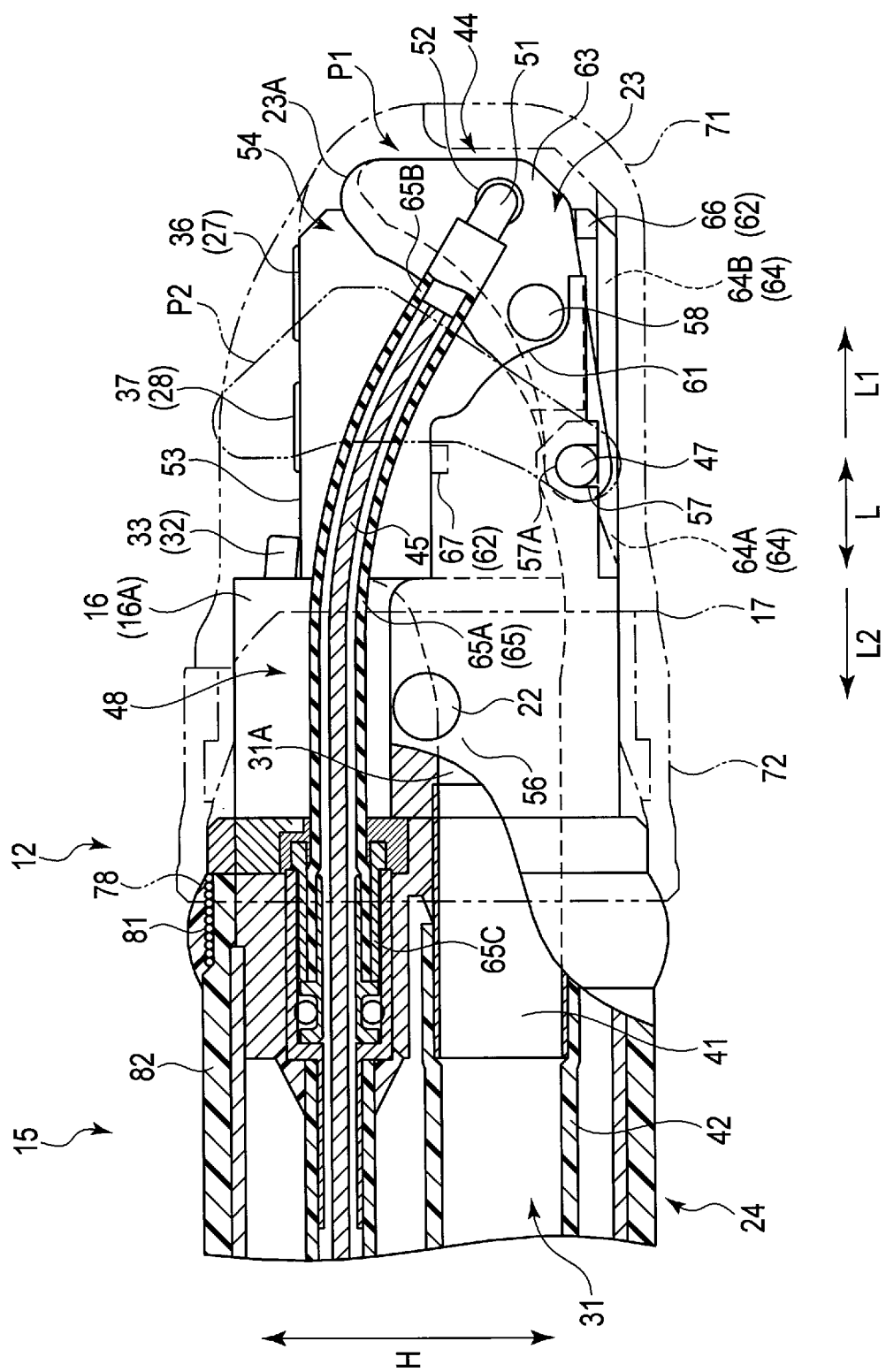
FIG. 12 is a cross-sectional view illustrating the endoscope system shown in FIG. 11, which is cut by a plane along the center axis C and is viewed from a lateral side.

The treatment instrument insertion channel 31 has a distal end opened in the distal structure portion 16 of the insertion section 15 of the endoscope 12 (see FIG. 5, 12), and has a proximal end opened near a proximal portion of the tube portion 25 of the insertion section 15, or opened in the operation section 18. Here, as illustrated in FIG. 1, an opening (not shown) of the proximal end of the treatment instrument insertion channel 31 is provided in the operation section 18, and a forceps tap 38 is detachably attached to this opening via a mouthpiece. As illustrated in FIG. 12, a distal end of a tube 42 of the treatment instrument insertion channel 31 is fixed to the distal structure portion 16 via a mouthpiece 41. Note that, as illustrated in FIG. 1, the tube 42 of the treatment instrument insertion channel 31 is branched into a suction conduit 39, for example, in the inside of the operation section 18. The suction conduit 39 is coupled to the second button 35. By a pressing operation of the second button 35, sucked matter is discharged from an opening portion 31A at the distal end of the treatment instrument insertion channel 31 via the mouthpiece 41, tube 42, suction conduit 39 and universal cord 21.

In this embodiment, the distal structure portion 16 is formed as such a side-viewing type that the direction of observation is different from a direction along the longitudinal direction L of the insertion section 15. The endoscope 12 includes a direction-changing mechanism 44 which properly changes the direction of a distal end of a treatment instrument 43 or the like, which is passed through the treatment instrument insertion channel 31, in the distal structure portion 24, thereby enabling observation within the view field.

Figure 5:
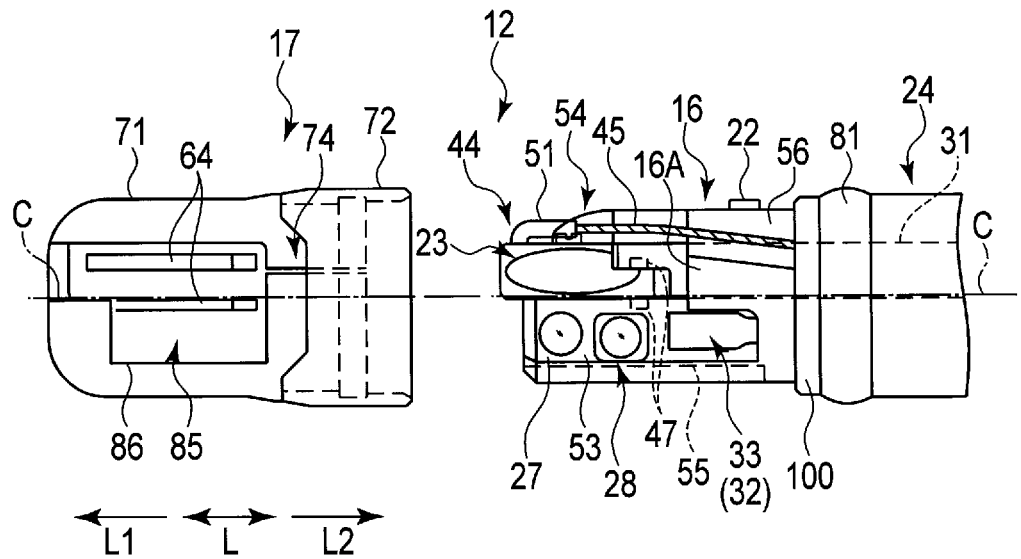
FIG. 5 is a plan view illustrating a step of attaching the cover to the distal structure portion illustrated in FIG. 2.

The direction-changing mechanism 44 has a distal end near the distal structure portion 16 of the insertion section 15 of the endoscope 12, and has a proximal end in the operation section 18. As illustrated in FIG. 1, FIG. 3, FIG. 5, etc., the direction-changing mechanism 44 includes, in the named order from the distal end toward the proximal end of the insertion section 15, a pivot base 23 (treatment instrument raising base; raising base); an elongated (linearly extending) wire 45 (pulling member); and a lever 46. The pivot base 23 is formed in a substantially triangular shape or a boomerang shape. The pivot base 23 is supported on the distal structure portion 16 via a rotational shaft 47, and can pivotally move (raise) the treatment instrument 43 at the distal end of the insertion section 15. A distal end of the wire 45 is supported by the pivot base 23, and a proximal end of the wire 45 is supported by the lever 46. As illustrated in FIG. 3, the wire 45 (pulling member) is connected to the pivot base 23 in a wire moving section 48 provided in the distal structure portion 16, and can remotely operate the pivot base 23. As illustrated in FIG. 3, an operating shaft portion 51, which is formed in an "L" shape, is provided at the distal end of the wire 45. The operating shaft portion 51 is fitted in a receiving portion 52 such that the operating shaft portion 51 is rotatable relative to the receiving portion 52 of the pivot base 23 and does not drop from the receiving portion 52.

As illustrated in FIG. 3, FIG. 5, etc., the distal structure portion 16 includes a block-shaped main body 16A. The main body 16A is formed of, for example, a rigid material such as stainless steel, in a substantially columnar shape. As illustrated in FIG. 5, in the main body 16A, a planar portion 53, a storage portion 54 (storage space), the wire moving section 48 (wire moving space), a guide groove 55 and a pin fixing portion 56 are formed. In the main body 16A, a center axis C is defined. In the description below, it is assumed that the above-described longitudinal direction L agrees with the center axis C.

As illustrated in FIG. 3, FIG. 12, etc., the main body 16A is provided with the illumination window 36 at the distal end of the illumination optical system 27; the observation window 37 at the distal end of the observation optical system 28; and a distal portion of the tube 42 of the treatment instrument insertion channel 31. Thus, the distal structure portion 16 is formed of the main body 16A, the illumination window 36, the observation window 37, and the distal portion of the tube 42. The pivot base 23 at the distal end portion of the direction-changing mechanism 44 is rotatably attached to the main body 16A.

As illustrated in FIG. 3, FIG. 5 and FIG. 12, the main body 16A includes the planar portion 53 in which the illumination window 36 and observation window 37 are fixed; the storage portion 54 which pivotably stores the pivot base 23; the opening portion 31A which communicates with the storage portion 54 and with the treatment instrument insertion channel 31, and guides the treatment instrument 43 to the pivot base 23; a bearing 57 which rotatably holds the rotational shaft 47 of the pivot base 23; a guide portion 61 which guides a preventing portion 58 (to be described later) of the pivot base 23; and a rotation restriction portion 62 which is provided to neighbor the guide portion 61 and restricts the range of rotation of the pivot base 22. As illustrated in FIG. 12, the distal end of the treatment instrument insertion channel 31 is fixed in the opening portion 31A. Note that, as illustrated in FIG. 3, the wire moving section 48, which is continuous with the storage portion 54 and moves the wire 45, is formed on the proximal side of the storage portion 54.

It is assumed that the planar portion 53 of the main body 16A is parallel to the longitudinal direction L. As illustrated in FIG. 3 and FIG. 5, on the planar portion 53 of the main body 16A, the illumination window 36 is arranged on the distal side, and the observation window 37 is arranged adjacent to the illumination widow 36 on the proximal side. Note that the nozzle 33 is provided on the proximal side of the observation window 37. The nozzle 33 is directed toward the observation window 37 and illumination widow 36. The nozzle 33 can discharge a liquid, such as physiological saline, toward the observation window 37 and illumination widow 36, and can blow away, by air, a deposit on the observation window 37 and illumination widow 36.

As illustrated in FIG. 12, the bearing 57 is provided to be recessed from a peripheral part (outer surface) of the distal structure portion 16, such that the bearing 57 receives the rotational shaft 47 of the pivot base 23 (to be described later). The bearing 57 has a substantially "U" shape, and can support the rotational shaft 47 in the inside thereof. In other words, it can be said that the bearing 57 has a groove shape. The dimension of the bearing 57 in the longitudinal direction (L direction) is equal to or slightly greater than the dimension of the rotational shaft 47 in the longitudinal direction (L direction). Thus, the bearing 57 can determine the position of the rotational shaft 47 with respect to the longitudinal direction L. In the state in which the cover 17 is removed from the distal structure portion 16, the rotational shaft 47 can be lifted relative to a bottom A of the bearing 57.

As illustrated in FIG. 3 and FIG. 5, the storage portion 54 is arranged in a direction perpendicular to the longitudinal direction L, relative to the planar portion 53. The storage portion 54 forms a space in which the pivot base 23 can rotate within a predetermined range. As illustrated in FIG. 12, the pivot base 23 is pivotable relative to the bearing 57 of the main body 16A, with the rotational shaft 47 functioning as the fulcrum. The pivot base 23 is a treatment instrument raising base which is rotatable about the rotational shaft 47 and raises (erects) the treatment instrument 43, which is inserted in the subject along the insertion section 15, relative to the insertion section 15.

Figure 13:
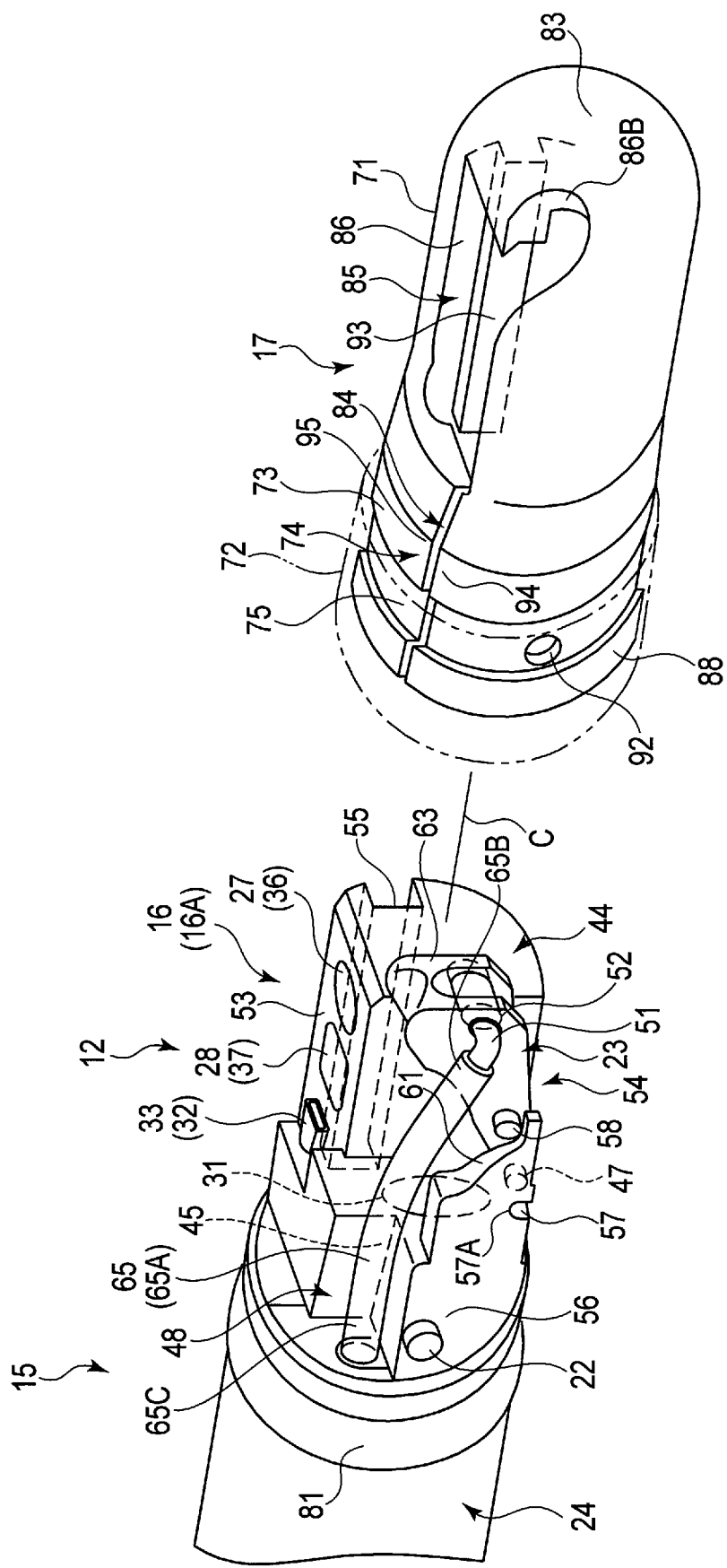
FIG. 13 is an exploded perspective view illustrating a state in which the cover is detached from the distal structure portion in the endoscope system illustrated in FIG. 11.

As illustrated in FIG. 3, FIG. 12 and FIG. 13, the pivot base 23 includes a pivot base body 63; the rotational shaft 47 which is formed as one body with, or formed integral with, the pivot base body 63; and a preventing portion 58 which prevents the rotational shaft 47 from dropping from the bearing 57 of the main body 16A. The rotational shaft 47 is held to be rotatable relative to the bearing 57 of the distal structure portion 16. The rotational shaft 47 is provided to project on both sides in a direction crossing the longitudinal direction L from the pivot base body 63 of the pivot base 23. Thus, the rotational shaft 47 of the pivot base 23 is rotatably supported in a so-called both-end support fashion, such that the rotational shaft 47 is clamped between the bearing 57 of the distal structure portion 16 and an alignment portion 64 (to be described later) of the cover 17. The bearing 57 and alignment portion 64 can determine the position of the rotational shaft 47 in a height direction H which crosses the longitudinal direction L. In the present embodiment, the preventing portion 58 is provided on the pivot base 23 side. Note that, although FIG. 12 and FIG. 13 correspond to a modification in which an elastic member 65 is disposed around the wire 45, the elastic member 65 is not present in the present embodiment and the wire 45 is exposed in the wire moving section 48.

The preventing portion 58 is composed of, for example, a screw (a head portion of a screw) which is fixed in a screw hole formed in the pivot base body 63 of the pivot base 23. However, the preventing portion 58 may be a pin or the like. In the state in which the cover 17 is removed from the distal structure portion 16, the preventing portion 58 cooperates with the guide portion 61 and wire 45, thereby setting to a predetermined dimension a distance (gap) of lifting of the rotational shaft 47 from the bottom A of the bearing 57. This predetermined dimension is properly set with respect to the height direction H of the distal structure portion 16, such that the rotational shaft 47 does not drop from the bearing 57 but a brush for cleaning can be passed through the gap. Thus, it is possible to prevent the rotational shaft 47 from dropping from the bearing 57, and to prevent the pivot base 23 from dropping from the distal structure portion 16.

A distal end of the wire 45 of the direction-changing mechanism 44 is supported by the pivot base 23. Note that the proximal end (not shown) of the wire 45 of the direction-changing mechanism 44 is supported by the lever 46 of the operation section 18. When the lever 46 is set in a most raised state illustrated in FIG. 1, the pivot base 23 is disposed in a fallen position P1 indicated by a solid line in FIG. 12. As the lever 46 is gradually pushed down, the wire 45 is pulled, and a distal-side end portion 23A of the pivot base 23, which is remote from the rotational shaft 47, is gradually raised with the rotational shaft 47 functioning as the fulcrum. Then, when the lever 46 is most pushed down, the pivot base 23 is disposed in a most raised position P2, as indicated by a two-dot-and-dash line in FIG. 12, As illustrated in FIG. 12, the guide portion 61 of the distal structure portion 16 is formed in an arcuate shape having a center at the bearing 57, in such a manner to guide the preventing portion 58 of the pivot base 23. The guide portion 61 can guide the preventing portion 58 when the pivot base 23 is rotated relative to the distal structure portion 16. The rotation restriction portion 62 is provided to neighbor the guide portion 61 and to be continuous with the guide portion 61. The rotation restriction portion 62 includes a first stopper 66 which restricts the rotational angle of the pivot base 23 on the fallen position P1 side of the pivot base 23, and a second stopper 67 which restricts the rotational angle of the pivot base 23 on the raised position P2 side of the pivot base 23. The first stopper 66 and second stopper 67 abut on pivot base 23, thereby restricting the rotational angle of the pivot base 23.

As illustrated in FIG. 3, FIG. 5 and FIG. 13, the main body 16A of the distal structure portion 16 includes, on an outer peripheral surface thereof, a guide groove 55 along the longitudinal direction L. The guide groove 55 neighbors the planar portion 53, but is formed on an opposite side to the storage portion 54 (i.e. the wire 45 and pivot base 23 of the direction-changing mechanism 44), with the planar portion 53 being interposed. It is preferable that the guide groove 55 is continuously formed from the distal end to proximal end of the main body 16A.

As illustrated in FIG. 3 and FIG. 5, the pin fixing portion 56 is formed on the outer peripheral surface of the main body 16A of the distal structure portion 16. It is preferable that the pin fixing portion 56 neighbors the wire moving section 48 and is formed substantially on the opposite side to the guide groove 55, with the center axis C of the main body 16A of the distal structure portion 16 being interposed. The engaging pin 22 is fixed on the pin fixing portion 56. The engaging pin 22 projects in a radial direction crossing the center axis C (a radial direction of the distal structure portion 16). The engaging pin 22 is formed in a columnar shape, but the shape of the engaging pin 22 is not limited to the columnar shape.

Figure 4:
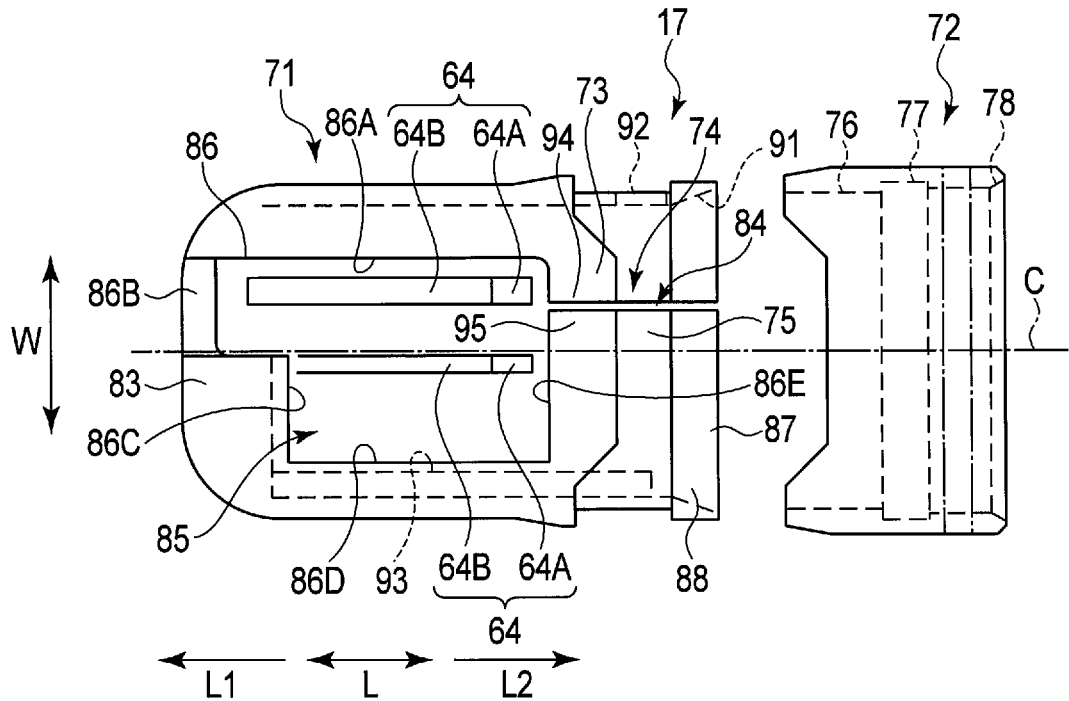
FIG. 4 is an exploded plan view illustrating a cover body and a covering portion of the cover illustrated in FIG. 2.

As illustrated in FIG. 2 and FIG. 4, the cover 17 includes a cover body 71 and a covering portion 72. The cover 17 is detachably attached to the outside of the distal structure portion 16. When the cover 17 is attached to the distal structure portion 16, the cover 17 constitutes a jacket which covers the distal structure portion 16. It is preferable that the cover body 71 and covering portion 72 are formed of a material with electrical insulation properties.

The covering portion 72 is formed of, for example, a material (synthetic rubber or the like) having rubber-like elasticity, in a cylindrical or annular shape. The covering portion 72 can cover at least that part of an annular portion 73, at which at least the dividing portion 74 is provided. In the state in which the covering portion 72 is attached to the cover body 71, the covering portion 72 is put in close contact with the outer periphery of the annular portion 73. In the present embodiment, the covering portion 72 annularly covers the annular portion 73.

As illustrated in FIG. 3 and FIG. 4, the covering portion 72 includes, on its inner peripheral surface, an annular projection portion 76 which is engaged in an engaging portion 75 (to be described later) of the cover body 71, and an annular engaging recess portion 77 in which a flange portion 88 is engaged. Thus, as illustrated in FIG. 2, the covering portion 72 is engaged with the annular portion 73 of the cover body 71. As illustrated in FIG. 4 and FIG. 5, the covering portion 72 includes a second skirt portion 78 on its inner peripheral surface. As illustrated in FIG. 3, etc., the second skirt portion 78 can be engaged with, and can be put in water-tight contact with, a bobbin portion 81 (raised portion) on the insertion section 15 side. The bobbin portion 81 is formed by annularly winding a thread around an outer peripheral part of a distal portion of the bending portion 24, and can fix a jacket 82 of the bending portion 24 to the distal structure portion 16. The surface of the bobbin portion 81 is coated with resin or the like. The second skirt portion 78 has a gradually decreasing thickness toward the proximal side along the longitudinal direction L, and has a gradually increasing inside diameter toward the proximal direction L2 side. In addition, the covering portion 72 is put in water-tight contact with an outer peripheral surface of a ring member 100 which is provided on the distal side of the bobbin portion 81 and is formed of an electrically insulating member.

The cover body 71 is formed of, for example, a synthetic resin material or the like in an integral cylindrical shape. The cover body 71 can be formed by injection molding or the like. As illustrated in FIG. 4, the cover body 71 includes a closing portion 83 provided on the distal direction L1 side; an annular portion 73 on the proximal direction L2 side; a slit 84 provided in the annular portion 73; a dividing portion 74 provided in the annular portion 73 in a manner to define the surrounding of the slit 84; an opening 85 provided in a substantially rectangular shape in a central portion of the cover body 71; an opening edge portion 86 which defines the surrounding of the opening 85; and a proximal edge portion 87 provided on the annular portion 73 and located at a proximal end in the longitudinal direction L. The closing portion 83 is formed in a cap shape (in a substantially hemispheric shape). In the state in which the annular portion 73 is attached to the distal structure portion 16, the annular portion 73 can surround the periphery of the distal structure portion 16. The opening 85 (opening edge portion 86) exposes the illumination window 36, observation window 37, nozzle 33 and pivot base 23 (treatment instrument raising base) of the distal structure portion 16 to the outside. The proximal edge portion 87 defines an outer edge on the proximal direction L2 side of the annular portion 73 (cover body 71).

As illustrated in FIG. 4, the opening edge portion 86 includes a right-side edge portion 86A which is provided on the right side; a U-shaped recess portion 86B which is continuous with the right-side edge portion 86A; a distal-side edge portion 86C which is continuous with the recess portion 86B; a left-side edge portion 86D which is continuous with the distal-side edge portion 86C and is provided on the left side; and a proximal-side edge portion 86E which is located on the proximal direction L2 side and is continuous with the right-side edge portion 86A and left-side edge portion 86D. The opening edge portion 86 forms a substantially closed loop by the right-side edge portion 86A, recess portion 86B, distal-side edge portion 86C, left-side edge portion 86D and proximal-side edge portion 86E. It is preferable that the right-side edge portion 86A and left-side edge portion 86D are parallel or substantially parallel to each other. It is preferable that the distal-side edge portion 86C and proximal-side edge portion 86E are parallel or substantially parallel to each other. Not only at a time when the pivot base 23 pivotally moves the treatment instrument 43, but also at all other times, the endoscope 12 exposes the pivot base 23 from the opening 85.

As illustrated in FIG. 4, the annular portion 73 includes, on its outer peripheral surface, an engaging portion 75 with which the covering portion 72 is engaged. The engaging portion 75 is formed at a position spaced apart toward the proximal direction L2 side from the proximal-side edge portion 86E of the opening edge portion 86. The annular portion 73 includes an annular flange portion 88 at a proximal end of the engaging portion 75. The annular flange portion 88 projects radially outward, relative to the engaging portion 75. A skirt portion 91, which has a gradually decreasing thickness toward the proximal direction L2 side along the longitudinal direction L, is formed on the inner periphery of the flange portion 88. The skirt portion 91 has a gradually increasing inside diameter toward the proximal direction L2 side.

As illustrated in FIG. 4, FIG. 5, FIG. 13, etc., an engaging portion 92 which is provided on the annular portion 73 and is engageable with the engaging pin 22; a restriction portion 93 which restricts the rotation of the cover 17 relative to the distal structure portion 16; and an alignment portion 64 which aligns the rotational shaft 47, are provided on an inner peripheral surface of the cover body 71. The engaging portion 92 is provided near the dividing portion 74. The engaging portion 92 may be formed in a through-hole shape via which the inner peripheral surface and outer peripheral surface of the cover body 71 communicate, or may be simply formed in a recess shape in the inner peripheral surface of the cover body 71.

The restriction portion 93 is provided on an opposite side to the engaging portion 92, with the dividing portion 74 being interposed. The restriction portion 93 is formed to be movable along the guide groove 55, and projects radially inward from the inner peripheral surface of the cover body 71. In addition, when the cover 17 is attached to the distal structure portion 16, the restriction portion 93 can be engaged with the guide groove 55 of the distal structure portion 16. It is preferable that the restriction portion 93 is formed from the vicinity of the distal end of the inner peripheral surface of the cover body 71 to the vicinity of the proximal end thereof. The restriction portion 93 can be formed in a proper shape. For example, it is preferable that the restriction portion 93 has a transverse cross section which is formed in a substantially rectangular shape in a manner to correspond to the shape of the guide groove 55. Besides, although not illustrated, the restriction portion 93 may be composed of a plurality of restriction portions which are mutually spaced apart at proper intervals.

As illustrated in FIG. 4, the alignment portion 64 is formed of a pair of alignment portions each extending in the longitudinal direction L. One of the alignment portions 64 has a greater dimension with respect to a width direction W crossing the longitudinal direction L than the other of the alignment portions 64. As illustrated in FIG. 12, when the cover 17 is attached to the distal structure portion 16, the alignment portion 64 aligns the rotational shaft 47. To be more specific, as illustrated in FIG. 5 and FIG. 12, when the cover 17 is attached to the distal structure portion 16 in a direction along the longitudinal direction L of the insertion section 15, the alignment portion 64 moves the rotational shaft 47 in a height direction H crossing the longitudinal direction L, and aligns the rotational shaft 47 in a predetermined position (bottom 57A) in the bearing 57.

As illustrated in FIG. 4 and FIG. 12, each of the alignment portions 64 includes a smooth inclined surface 64A which gradually projects in an inward direction (direction toward the center axis C) toward the closing portion 83, and a track 64B extending from the inclined surface 64A in the longitudinal direction L. The inclined surface 64A guides the rotational shaft 47 to a predetermined position (bottom 57A) in the bearing 57, when the cover 17 is attached to the distal structure portion 16. The track 64B pushes the rotational shaft 47 onto the bearing 57, when the cover 17 is attached to the distal structure portion 16. After the cover 17 was attached to the distal structure portion 16, the track 64B abuts on the rotational shaft 47 and holds the rotational shaft 47 in the predetermined position (bottom 57A) in the bearing 57.

As illustrated in FIG. 4, the dividing portion 74 (slit 84) is provided between the engaging portion 92 and restriction portion 93. The slit 84 is continuous with the opening edge portion 86 (proximal-side edge portion 86E) and the proximal edge portion 87. The dividing portion 74 (slit 84) extends, for example, in a direction along the longitudinal direction L, and divides the annular portion 73 in advance in this direction. The direction in which the dividing portion 74 (slit 84) extends is not limited to the direction along the longitudinal direction L, and the dividing portion 74 (slit 84) may have any shape if the slit 84 is continuous with the opening edge portion 86 (proximal-side edge portion 86E) and the proximal edge portion 87. For example, the direction in which the dividing portion 74 (slit 84) extends may be oblique to the direction along the longitudinal direction L.

The dividing portion 74 is provided in a position where the annular portion 73 is divided by the slit 84. The dividing portion 74 includes a first cylindrical wall portion 94 which is located on the side where the engaging portion 92 is provided, and a second cylindrical wall portion 95 which is located on the side where the restriction portion 93 is provided. The second cylindrical wall portion 95 is opposed to the first cylindrical wall portion 94, and is provided substantially parallel to the first cylindrical wall portion 94. In the present embodiment, a gap (i.e. slit 84) remains between the first cylindrical wall portion 94 and second cylindrical wall portion 95.

Referring to FIG. 4, FIG. 5, etc., the function of the cover 17 of the present embodiment will be described. The disassembled state of the cover 17, which is illustrated in FIG. 4, is changed to the state illustrated in FIG. 5 by attaching the covering portion 72 to the cover body 71. Then, as illustrated in FIG. 5, the cover 17 is attached to the distal structure portion 16. At this time, the restriction portion 93 of the cover 17 is engaged with the guide groove 55 of the main body 16A of the distal structure portion 16, and the cover 17 is moved along the longitudinal direction L.

In the endoscope 12, in the state in which the cover 17 is attached to the distal structure portion 16, the insertion section 15 is inserted into a tract such as a lumen cavity, and observation and a proper treatment are performed. Note that a part of the dividing portion 74 is covered and protected by the covering portion 72. Thus, for example, during the insertion of the insertion section 15 into the body or the like, or during a treatment, even if the cover 17 abuts on an inner wall of the tract or the like in the body, the cover does not drop from the distal structure portion 16.

Figure 6:
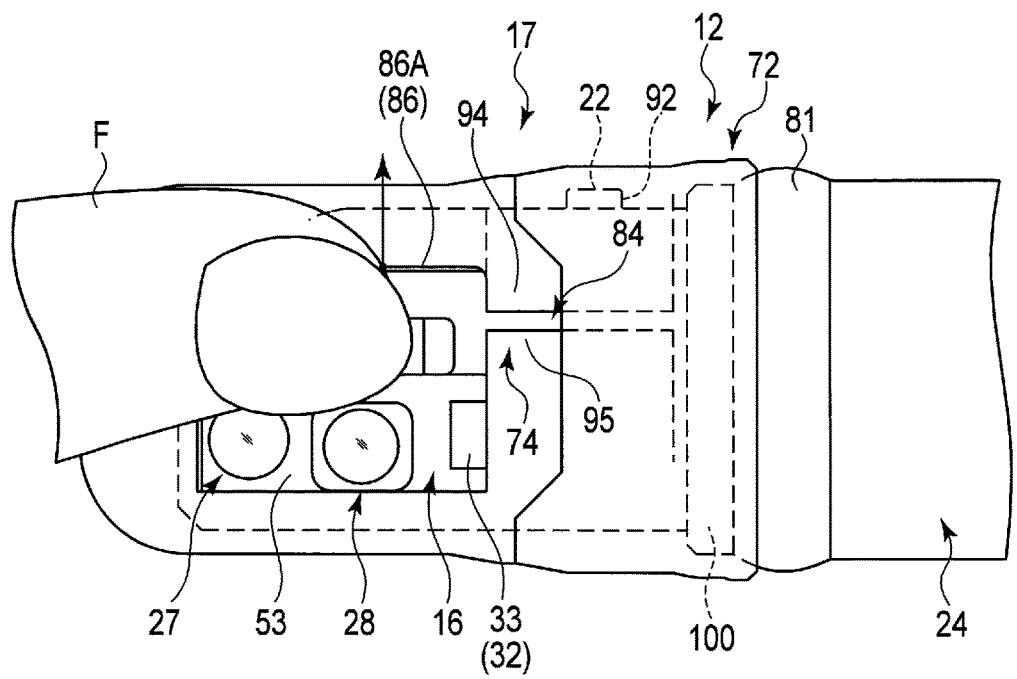
FIG. 6 is a plan view illustrating a step of releasing the engagement between an engaging portion and an engaging pin and detaching the cover from the distal structure portion, by applying force, by a finger, to an opening edge portion (right-side edge portion) of the cover illustrated in FIG. 2.

After the use of the endoscope 12, the cover 17 and covering portion 72 are removed from the distal structure portion 16. In the present embodiment, as illustrated in FIG. 4, etc., the annular portion 73 is divided in advance in the dividing portion 74. Thus, when a worker removes the cover 17, the worker does not need to perform such work as breaking a part of the annular portion 73. As illustrated in FIG. 6, etc., if the worker pushes the opening edge portion 86 (right-side edge portion 86A) by the finger F with a relatively weak force in a direction toward the engaging portion 92, the rotation of the cover 17 is restricted by the engagement between the guide groove 55 of the distal structure portion 16 and the restriction portion 93 of the cover body 71. If the worker continues the pushing, the cover body 71 and covering portion 72 elastically deform such that the slit 84 becomes wider (i.e. such that the first cylindrical wall portion 94 and second cylindrical wall portion 95 move away from each other), and the engagement between the engaging pin 22 and engaging portion 92 is relatively easily released. At this time, since no breakage occurs in the annular portion 73 and dividing portion 74, the worker does not need to apply great force to the cover 17.

In the state in which the engagement between the engaging pin 22 and engaging portion 92 is released in this manner, the cover 17 is pulled out to the distal direction L1 side of the longitudinal direction L, and thereby the cover 17 can be removed from the distal structure portion 16. At this time, since the annular portion 73 and dividing portion 74 include no broken part, the worker can safely perform the removing work. In addition, there is no need to perform a more bothersome removing work in order to prevent a broken part from damaging structural parts around the insertion section 15 and distal structure portion 16 of the endoscope 12. The cover 17, which was removed from the distal structure portion 16, is discarded.

In the state in which the cover 17 is removed, the endoscope 12 (the distal structure portion 16) is cleaned, disinfected and sterilized, and is reused. At this time, since the cover 17 is removed from the distal structure portion 16, the treatment instrument insertion channel 31 and direction-changing mechanism 44, as well as the vicinity of the illumination window 36 of the illumination optical system 27 and the vicinity of the observation window 37 of the observation optical system 28, are easily cleaned. Furthermore, since the rotational shaft 47 can be lifted from the bottom 57A of the bearing 57 at the time of cleaning, a brush or the like can easily be passed through the gap between the bearing 57 and rotational shaft 47. Thus, the cleaning performance of the distal structure portion 16 can be enhanced.

The endoscope 12 from which the cover 17 was removed, or, to be more specific, the insertion section 15 including the distal structure portion 16, the operation section 18 and the universal cord 21, are properly cleaned, disinfected and sterilized. By properly attaching a new cover 17 to the distal structure portion 16 of the endoscope 12 which was cleaned, disinfected and sterilized in this manner, the endoscope system 11 can be used for the next-time observation and treatment.

In the present embodiment, the first cylindrical wall portion 94 and second cylindrical wall portion 95 are linearly formed. Alternatively, one of the first cylindrical wall portion 94 and second cylindrical wall portion 95 may be provided with a projection portion, and the other of the first cylindrical wall portion 94 and second cylindrical wall portion 95 may be provided with a recess portion which has a complementary shape to the projection portion and can receive the projection portion. As the shape of the projection portion, the shape of a first engaging portion 109 of a fifth modification in FIG. 22 can be adopted. Similarly, as the shape of the recess portion, the shape of a second engaging portion 110 of the fifth modification illustrated in FIG. 22 can be adopted. A slit 84 remains between the projection portion and recess portion, and an overlapping portion 106, which will be described later, is not formed between the first cylindrical wall portion 94 and second cylindrical wall portion 95. Also when this shape is adopted, it is possible to prevent the position of the second cylindrical wall portion 95 from being greatly displaced from the first cylindrical wall portion 94 in the longitudinal direction L when external force is applied.

As described above, according to the endoscope system 11 of the present embodiment, the following can be said. The cover 17 is attached to the distal structure portion 16 of the insertion section 15 of the endoscope 12, and the cover 17 includes the cover body 71 and covering portion 72. The cover body 71 includes the opening edge portion 86 which defines the surrounding of the opening 85 that exposes a part of the distal structure portion 16; the annular portion 73 which surrounds the periphery of the distal structure portion 16; the proximal edge portion 87 provided on the annular portion 73 and located at the proximal end in the longitudinal direction L of the insertion section 15; and the dividing portion 74 provided in the annular portion 73 in a manner to define the slit 84 that is continuous with the opening edge portion 86 and proximal edge portion 87. The covering portion 72 covers that part of the annular portion 73, at which at least the dividing portion 74 is provided.

According to this configuration, the slit 84, which is continuous with the opening edge portion 86 and proximal edge portion 87, and the dividing portion 74, which defines the slit 84, are provided in advance in the cover body 71. Thus, when the cover 17 is removed, there is no need to break a part of the annular portion 73. Therefore, there is no need to additionally use a jig, a tool or the like in order to remove the cover 17, and it is possible to remove the cover 17 from the distal structure portion 16 with a relatively weak force by using the finger F. Thereby, the convenience for the worker who performs the removing work of the cover 17 can remarkably be improved. In addition, according to the above configuration, since a sharp broken part is not formed in the annular portion 73, the worker can safely perform the work. Besides, there is no need to perform a more bothersome removing work in order to prevent a broken part from damaging the distal structure portion 16 or structural parts therearound when the cover 17 is removed from the distal structure portion 16. Moreover, since the dividing portion 74 can be covered by the covering portion 72, the dividing portion 74 can be protected by the covering portion 72. Thereby, the slit 84 does not open when not intended by the user, and it is possible to further reduce the possibility of the occurrence of such a problem that the cover 17 drops from the distal structure portion 16 while the endoscope system 11 is being used.

The endoscope system 11 includes the cover 17; and the endoscope 12 including the insertion section 15 and the distal structure portion 16 which is provided on the distal side of the insertion section 15, and to the outside of which the cover 17 is attached. According to this configuration, since the endoscope system 11 including the cover 17 that is easy to attach/detach can be realized, the convenience for the worker who performs a cleaning work can remarkably be improved.

In the endoscope system 11, the distal structure portion 16 of the endoscope 12 includes the treatment instrument raising base which changes the direction of the distal side of the treatment instrument which is inserted in the insertion section 15, and the opening 85 exposes the treatment instrument raising base to the outside. According to this configuration, the opening 85, which exposes the treatment instrument raising base, and the opening edge portion 86 can also be utilized to remove the cover 17. Thus, the endoscope system 11, which includes the cover 17 that is simple in structure and is easy to remove, can be realized.

In this case, the covering portion 72 annularly covers the annular portion 73. According to this configuration, sufficient strength can be given to the covering portion 72. Thereby, it is possible to effectively prevent the cover 17 from dropping from the distal structure portion 16 at a timing not intended by the user.

The covering portion 72 has elasticity and is put in close contact with the outer periphery of the annular portion 73. According to this configuration, when the worker attaches/detaches the cover 17 to/from the distal structure portion 16, the worker can easily elastically deform the covering portion by the force of a finger F. Thereby, there is no need to use a special jig, tool or the like when attaching/detaching the cover 17, and the convenience for the worker can remarkably be improved.

The cover body 71 includes the engaging portion 92, which is engaged with the distal structure portion 16, near the dividing portion 74. By the slit 84 being opened, the engagement between the engaging portion 92 and distal structure portion 16 is released. According to this configuration, since the engaging portion 92 is located near the dividing portion 74, the worker can easily release the engagement between the engaging portion 92 of the cover body 71 and the distal structure portion 16 by pushing a part of the opening edge portion 86 in a manner to open the slit 84 in the removing work of the cover 17. Thereby, the removing work of the cover 17 can easily be performed, and the convenience for the worker can further be improved.

The cover body 71 includes the restriction portion 93 on the opposite side to the engaging portion 92, with the dividing portion 74 being interposed. The restriction portion 93 is engaged with the distal structure portion 16, thereby restricting the rotation of the cover body 71 relative to the distal structure portion 16.

According to this configuration, the rotation of a part of the cover body 71 can be restricted by the restriction portion 93. Thereby, the cover 17 does not rotate when the worker elastically deforms the cover 17 by hooking the finger F on a part of the opening edge portion 86 in order to remove the cover 17 from the distal structure portion 16. Since the restriction portion 93 restricts the rotation of the cover body 71 in this manner, the worker can elastically deform the cover 17 with a relatively weak force. Thereby, the convenience for the worker, who performs the removing work of the cover 17, can be improved.

Figure 7:
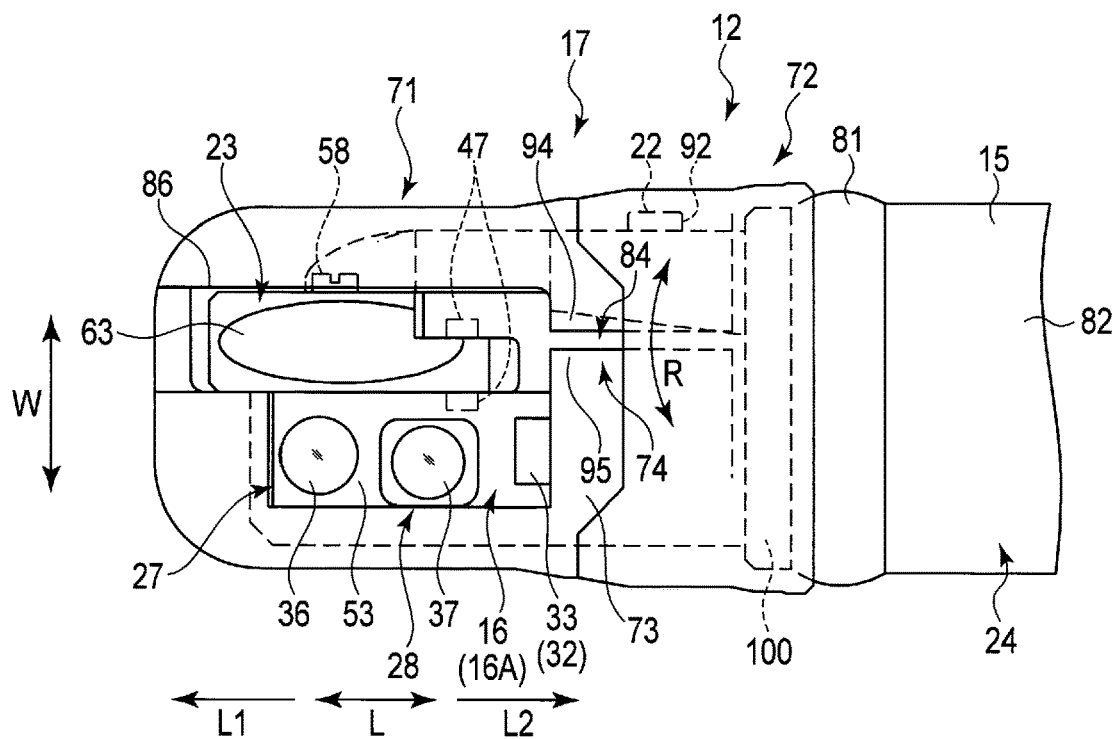
FIG. 7 is a plan view illustrating a surrounding of a cover of an endoscope system of an exemplary embodiment.

Referring to FIG. 7, a first modification of the endoscope system 11 will be described. The endoscope system 11 of the first modification is different with respect to the width of the slit 84 which is formed in the annular portion 73 of the cover 17.

In the present modification, with respect to the width direction W crossing the longitudinal direction L, the dimension (width) of the slit 84 is set to be greater than in the first embodiment. Thus, with respect to the width direction W, the distance between the first cylindrical wall portion 94 and second cylindrical wall portion 95 of the dividing portion 74, which defines the surrounding of the slit 84, is also greater than in the first embodiment.

According to the endoscope system 11 of the present modification, too, substantially the same advantageous can be exhibited. Further, according to this modification, since the width of the slit 84 formed in the annular portion 73 of the cover 17 is set to be large, the cover 17 can be removed from the distal structure portion 16, not only by hooking the finger on the opening edge portion 86 (right-side edge portion 86A), but also by directly hooking the finger on the dividing portion 74. In addition, even if the cover body 71 bends in a circumferential direction R of the cover 17 by external force, such bending can be absorbed by the slit 84 having the large width. Moreover, by adopting the slit 84 having the large width, the strictness of the tolerance with respect to the width of the slit 84 at the time of manufacture can be relaxed. Thereby, the yield of covers 17 can be improved, and the manufacturing cost can be reduced.

Figure 8:
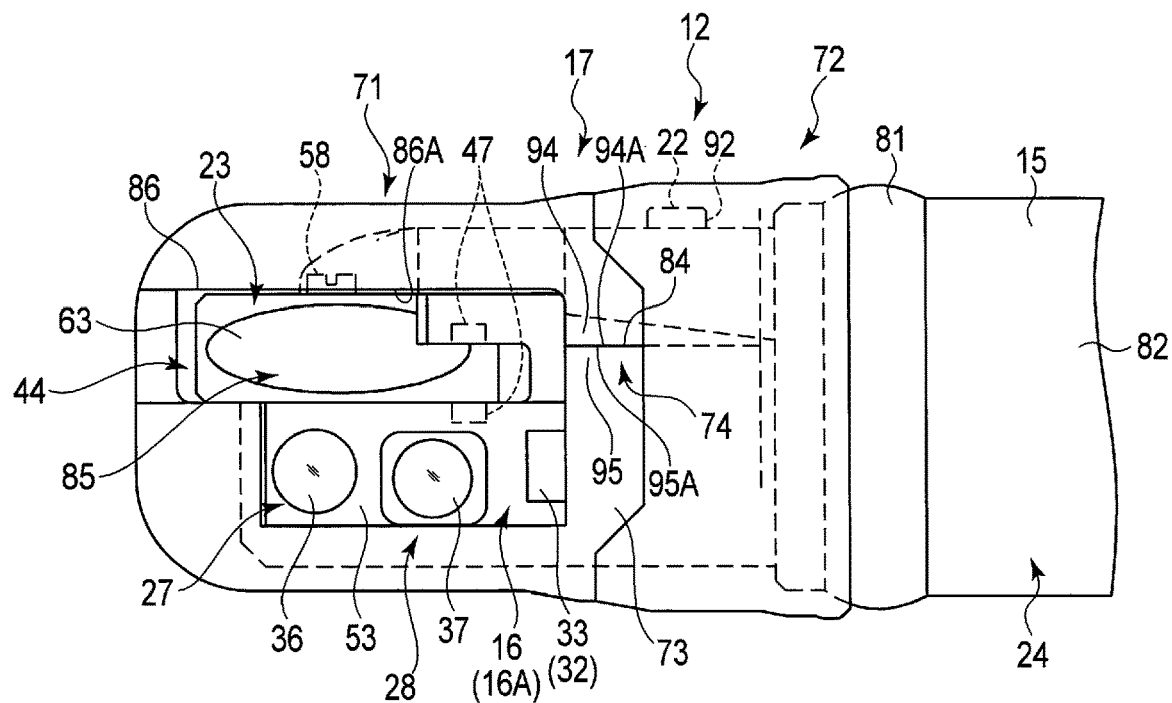
FIG. 8 is a plan view illustrating a surrounding of a cover of an endoscope system of an exemplary embodiment.

Referring to FIG. 8, a second modification of the endoscope system 11 will be described. The endoscope system 11 of the second modification is different from the first embodiment with respect to the width of the slit 84 which is formed in the annular portion 73 of the cover 17.

In the present modification, in the normal state, the dimension of the slit 84 with respect to the width direction W is set to substantially zero. Thus, the first cylindrical wall portion 94 of the dividing portion 74, which defines the surrounding of the slit 84, abuts on the second cylindrical wall portion 95.

According to the endoscope system 11 of the present modification, too, substantially the same advantageous effects can be exhibited. Further, according to this modification, since the first cylindrical wall portion 94 of the dividing portion 74 is formed so as to abut on the second cylindrical wall portion 95, frictional force or holding force (pressure) can be exhibited between the first cylindrical wall portion 94 and second cylindrical wall portion 95. Thereby, for example, even when external force is applied in such a direction that the position of the second cylindrical wall portion 95 is displaced from the first cylindrical wall portion 94, the original shape can be maintained to some extent by the interaction between the first cylindrical wall portion 94 and second cylindrical wall portion 95. Thereby, a decrease in strength of the cover 17 due to the provision of the slit 84 can be suppressed as much as possible.

In addition, according to the present modification, in the correct attachment state, the first cylindrical wall portion 94 and second cylindrical wall portion 95 abut on each other. Thus, if a gap occurs between the first cylindrical wall portion 94 and second cylindrical wall portion 95, the user can recognize a state (defective attachment state) in which the cover 17 is not correctly attached to the distal structure portion 16. In a further modification of the present modification, an index for easier recognition of the defective attachment state of the cover 17 may be provided on the distal structure portion 16 or cover 17 itself. In an example of the index, a colored area, which is colored with a warning color such as yellow or red, may be provided at that position of the distal structure portion 16, which corresponds to the dividing portion 74. In another example of the index, a colored area, which is colored with a warning color such as yellow or red, may be provided on at least one of the first cylindrical wall portion 94 (a first edge 94A that is an end face of the first cylindrical wall portion 94) and second cylindrical wall portion 95 (a second edge 95A that is an end face of the second cylindrical wall portion 95) of the cover body 71. By adopting these configurations, when a gap occurs between the first cylindrical wall portion 94 and second cylindrical wall portion 95 in the defective attachment state, this gap can be made conspicuous by the colored area (index).

Figure 9:
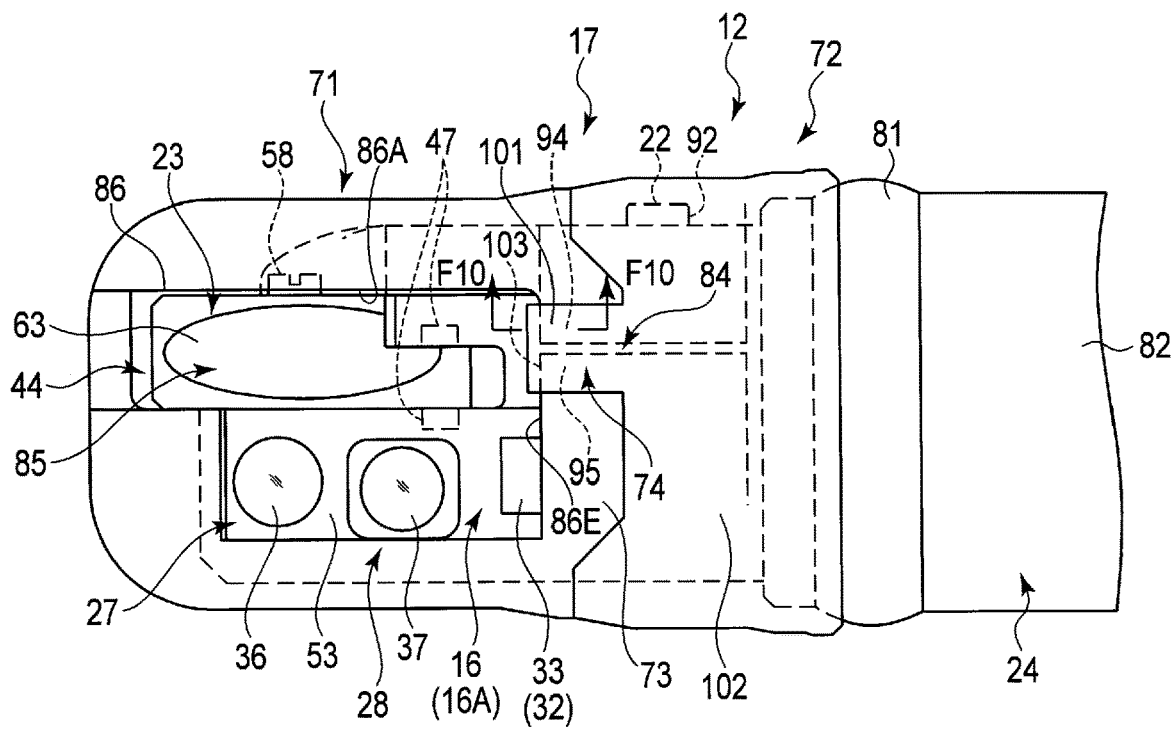
FIG. 9 is a plan view illustrating a surrounding of a cover of an endoscope system of an exemplary embodiment.
Figure 10:
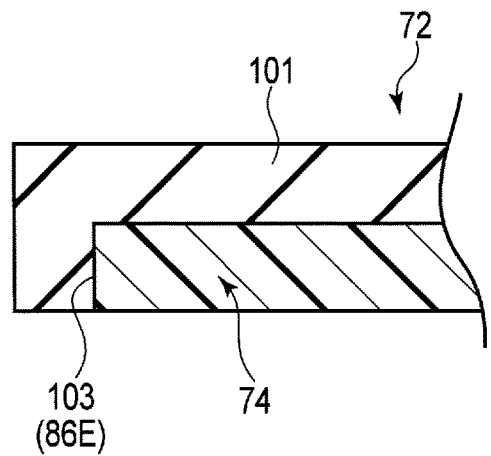
FIG. 10 is a cross-sectional view illustrating a cover body and a covering portion which are cut at a position of line F10-F10 in FIG. 9.

Referring to FIG. 9 and FIG. 10, a third modification of the endoscope system 11 will be described. The endoscope system 11 of the third modification is different in that the covering portion 72 is provided with a projection portion 101.

As illustrated in FIG. 10, the covering portion 72 covers the entirety of the dividing portion 74 (slit 84). The covering portion 72 includes a covering portion body 102, and the projection portion 101 which projects from the covering portion body 102. The projection portion 101 projects from the covering portion body 102 in an L shape in cross section. As illustrated in FIG. 9, the projection portion 101 covers the dividing portion 74 and the proximal-side edge portion 86E near the dividing portion 74. To be more specific, the projection portion 101 covers a dividing end face 103 that is an end face located at that part of the proximal-side edge portion 86E, which corresponds to the dividing portion 74. Note that the part of the proximal-side edge portion 86E, which corresponds to the dividing portion 74, forms an angle in the vicinity of the slit 84, and it is preferable, therefore, to cover and protect this part by the projection portion 101 as in the present modification. In addition, according to this configuration, even when external force acts in the vicinity of the dividing portion 74, the projection portion 101 can suppress, to some extent, deformation of the dividing portion 74 in a direction in which the slit 84 widens. Thereby, it is possible to prevent such a problem that the slit 84 widens at a time not intended by the user, and the cover 17 drops from the distal structure portion 16.

According to the present modification, the opening edge portion 86 includes the proximal-side edge portion 86E provided at a position neighboring the dividing portion 74, and the covering portion 72 covers the proximal-side edge portion 86E. According to this configuration, the proximal-side edge portion 86E can be protected by the covering portion 72. Thereby, even when external force acts in the vicinity of the dividing portion 74, the dividing portion 74 does not deform in the direction in which the slit 84 widens, and it is possible to prevent such a problem that the cover 17 drops from the distal structure portion 16.

Figure 11:
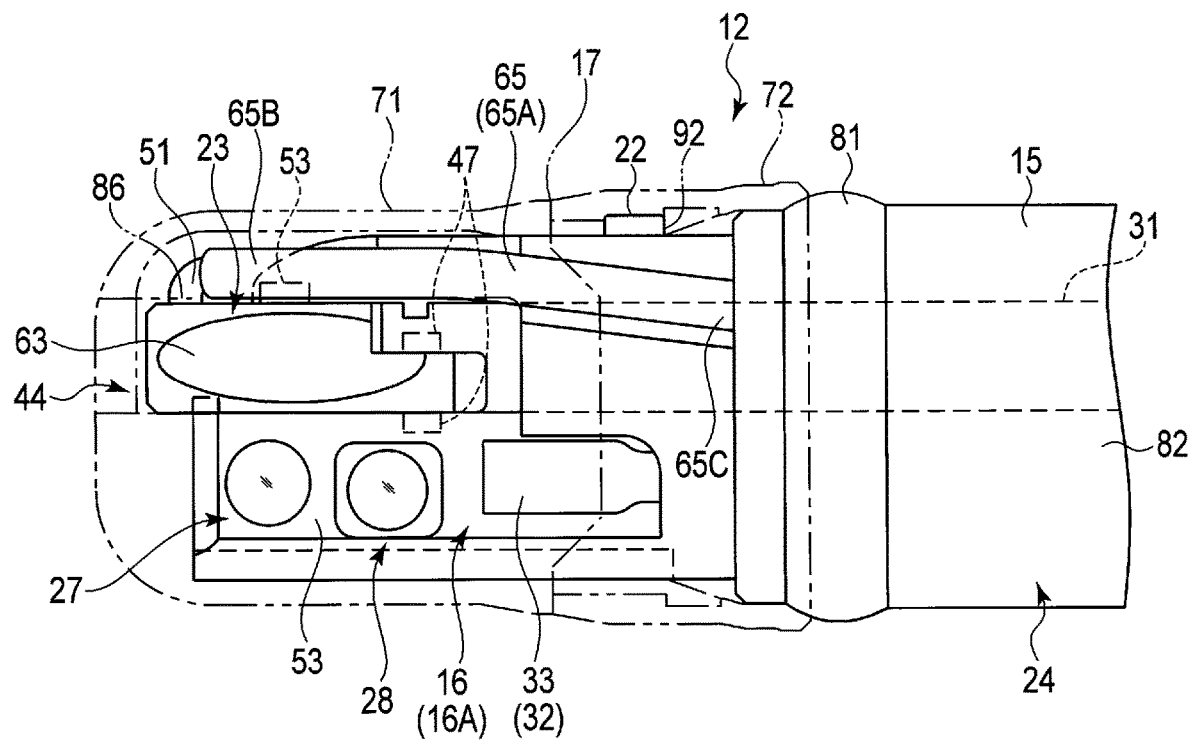
FIG. 11 is a plan view illustrating a surrounding of a cover of an endoscope system of an exemplary embodiment.

Referring to FIG. 11 to FIG. 13, a fourth modification of the endoscope system will be described. The endoscope system 11 of the fourth modification is different in that an elastic member 65 is provided around the wire 45.

As illustrated in FIG. 12, the elastic member 65 is formed of a material, such as rubber, in a cylindrical shape (tubular shape). An exposed part of the wire 45 can be passed through the inside of the elastic member 65. The elastic member 65 includes an elastic member body 65A; one end 65B which is water-tightly fixed to the pivot base 23 side on the distal direction L1 side of the longitudinal direction L; and the other end 65C which is water-tightly fixed to the distal structure portion 16 on the proximal direction L2 side of the longitudinal direction L. The elastic member 65 prevents liquid or gas from entering the inside of the insertion section 15 along the wire 45, to be more specific, the inside of the tube portion 25 of the insertion section 15. Both ends of the elastic member 65 are water-tightly connected to the pivot base 23 and the distal structure portion 16. The one end of the elastic member 65 is fixed, via an adhesive or the like, to that end portion of the operating shaft portion 51, which projects from the pivot base 23, but the fixing method is not limited to this. Although the other end 65C is water-tightly connected to the distal structure portion 16 via a mouthpiece 41 which is accommodated in the distal structure portion 16, the other end 65C may be water-tightly connected to the distal structure portion 16 by other methods.

According to the present modification, too, substantially the same advantageous effects can be exhibited. Further, since the cover 17 can be removed without involving breakage of the annular portion 73, no broken part occurs. Thus, when the cover 17 is removed, there is no concern that the elastic member 65 is damaged by the broken part.

Figure 14:
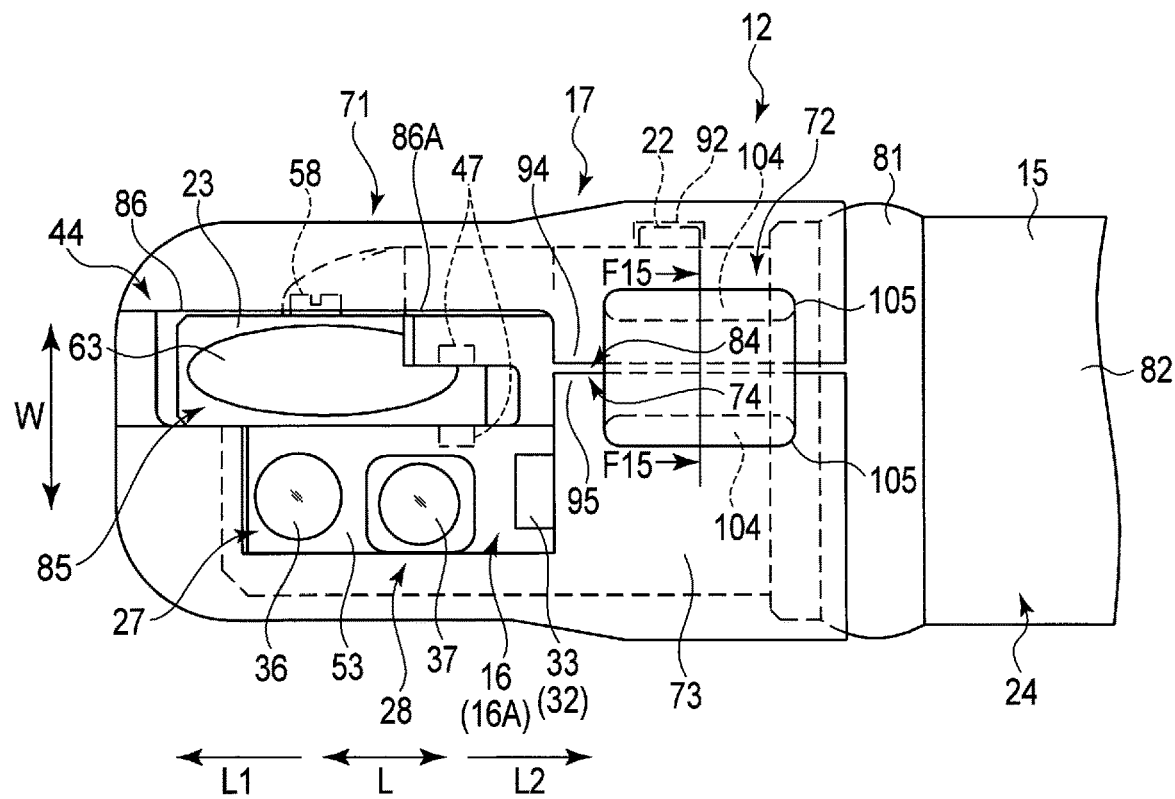
FIG. 14 is a plan view illustrating a surrounding of a cover of an endoscope system of an exemplary embodiment.
Figure 15:
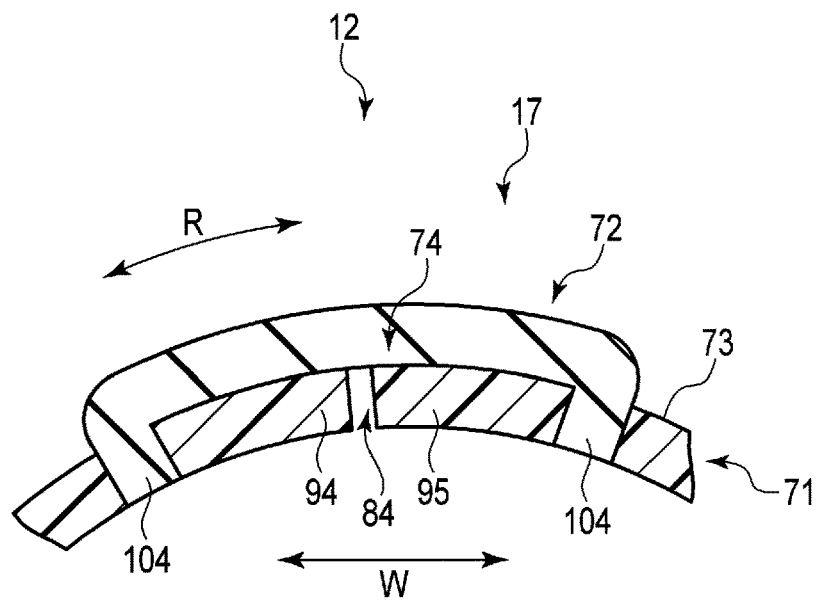
FIG. 15 is a cross-sectional view illustrating a cover body and a covering portion which are cut at a position of line F15-F15 in FIG. 14.

Referring to FIG. 14 and FIG. 15, a fifth modification of the endoscope system 11 will be described. The endoscope system 11 of the fifth modification is different with respect to the shape of the covering portion 72 and the shape of a part of the cover body 71.

The cover 17 includes a cover body 71 and a covering portion 72. The covering portion 72 is formed of, for example, a material (synthetic rubber or the like) having rubber-like elasticity, and is formed in a shape of a substantially rectangular small piece, as illustrated in FIG. 14. As illustrated in FIG. 15, the covering portion 72 includes a pair of insertion portions 104 in both end portions in a circumferential direction R or a width direction W of the cover 17. Each of the insertion portions 104 is formed in a projection shape projecting in a radial direction of the distal structure portion 16 from the body portion of the covering portion 72 toward the cover body 71. Each of the insertion portions 104 can be inserted in a receiving portion 105 (to be described later).

In the state in which the covering portion 72 is fixed to the cover body 71 via the insertion portions 104, the covering portion 72 can cover a part of the dividing portion 74 and protect the dividing portion 74. The covering portion 72 can function as a protection wall which protects the dividing portion 74. The covering portion 72 is provided in a manner to extend over both the first cylindrical wall portion 94 and second cylindrical wall portion 95 of the dividing portion 74. The covering portion 72 can also function as a stopper which prevents the slit 83 (the gap between the first cylindrical wall portion 94 and second cylindrical wall portion 95) from opening accidentally.

The cover body 71 includes a closing portion 83 provided on the distal direction L1 side; an annular portion 73 provided on the proximal direction L2 side; a slit 84 provided in the annular portion 73; a dividing portion 74 provided in the annular portion 73 in a manner to define the surrounding of the slit 84; an opening 85 provided in a substantially rectangular shape; an opening edge portion 86 which defines the surrounding of the opening 85; and a proximal edge portion 87 which defines an outer edge on the proximal direction L2 side of the annular portion 73 (cover body 71).

In this modification, the engaging portion 75 is not formed on the outer peripheral surface of the annular portion 73. In the present modification, the cover body 71 is provided with a pair of receiving portions 105 in place of the engaging portion 75. The paired receiving portions 105 are provided on both sides between which the dividing portion 74 (slit 84) is interposed. The insertion portions 104 of the covering portion 72 are inserted in the receiving portions 105. By the engagement between the receiving portions 105 and insertion portions 104, the covering portion 72 is detachably attached to the cover body 71. In the present modification, the receiving portion 105 is formed of, for example, a through-hole which penetrates the annular portion 73, but the shape of the receiving portion 105 is not limited to this. Needless to say, the receiving portion 105 may be formed as a recess portion which is recessed from the other part of the outer peripheral surface of the annular portion 73. A skirt portion 91, which has a gradually decreasing thickness toward the proximal direction L2 side along the longitudinal direction L, is formed on the inner periphery of the annular portion 73.

An engaging portion 92 which is engageable with the engaging pin 22, a restriction portion 93 which restricts the rotation of the cover 17 relative to the distal structure portion 16, and an alignment portion 64 which aligns the rotational shaft 47, are provided on an inner peripheral surface of the annular portion 73 of the cover body 71.

According to the present modification, the cover body 71 includes the paired receiving portions 105 provided on both sides between which the dividing portion 74 is interposed, and the covering portion 72 includes the paired insertion portions 104 which can be inserted in the paired receiving portions 105. According to this configuration, even when external force acts in the vicinity of the dividing portion 74, the dividing portion 74 can be protected by the covering portion 72 having a shape that is not limited to an annular shape. By this configuration, it is possible to prevent such a problem that the slit 84 opens at a time not intended by the user, and the cover 17 drops from the distal structure portion 16 while the endoscope system 11 is being used.

Figure 17:
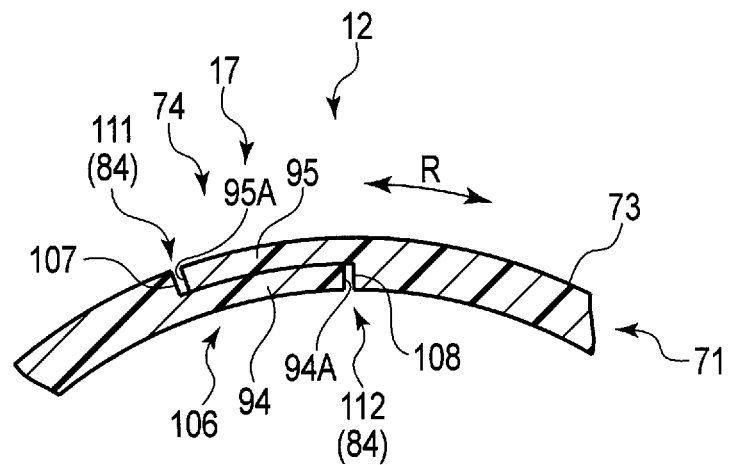
FIG. 17 is a cross-sectional view illustrating a cover body and a covering portion which are cut at a position of line F17-F17 in FIG. 16.

Referring to FIG. 16 and FIG. 17, another exemplary embodiment of the endoscope system 11 will be described. The endoscope system 11 differs with respect to the shape of the dividing portion 74 of the cover body 71. Hereinafter, different parts from will mainly be described, and illustrations or descriptions of parts common to previously described embodiments will be omitted.

The cover body 71 includes a closing portion 83 provided on the distal direction L1 side; an annular portion 73 provided on the proximal direction L2 side; a slit 84 provided in the annular portion 73; a dividing portion 74 provided in the annular portion 73 in a manner to define the surrounding of the slit 84; an opening 85 provided in a substantially rectangular shape; an opening edge portion 86 which defines the surrounding of the opening 85; and a proximal edge portion 87 which defines an outer edge on the proximal direction L2 side of the annular portion 73 (cover body 71).

An engaging portion 92 which is provided in the annular portion 73 and is engageable with the engaging pin 22, a restriction portion 93 which restricts the rotation of the cover 17 relative to the distal structure portion 16, and a pair of alignment portions 64 which align the rotational shaft 47, are provided on an inner peripheral surface of the cover body 71.

As illustrated in FIG. 16, the slit 84 is continuous with the opening edge portion 86 (proximal-side edge portion 86E) and the proximal edge portion 87, and the slit 84 is formed in a closed shape in the normal state. The dividing portion 74 (slit 84) divides the annular portion 73 in advance, for example, in a direction along the longitudinal direction L, but the direction in which the dividing portion 74 (slit 84) extends is not limited to this direction. The dividing portion 74 (slit 84) may have any shape, and may be, for example, oblique to the longitudinal direction L.

The dividing portion 74 is provided in a position where the annular portion 73 is divided by the slit 84. The dividing portion 74 includes a first cylindrical wall portion 94 which is located on the side where the engaging portion 92 is provided, and a second cylindrical wall portion 95 which is located on the side where the restriction portion 93 is provided. As illustrated in FIG. 17, at least a part of the first cylindrical wall portion 94 overlaps at least a part of the second cylindrical wall portion 95 with respect to the circumferential direction R of the cover 17. When the cover body 71 is viewed from the outside, the first cylindrical wall portion 94 and second cylindrical wall portion 95 have substantially rectangular shapes. The second cylindrical wall portion 95 overlaps the upper side of the first cylindrical wall portion 94. Thus, an overlapping portion 106 is formed in a part where the first cylindrical wall portion 94 and second cylindrical wall portion 95 of the cover body 71 (annular portion 73) overlap.

As illustrated in FIG. 17, each of the first cylindrical wall portion 94 and second cylindrical wall portion 95 is formed to have substantially half the thickness of the other part of the cover body 71. In the present embodiment, although substantially the entirety of the first cylindrical wall portion 94 is configured to overlap the second cylindrical wall portion 95, the mode of the overlapping may be freely set. Needless to say, for example, substantially half the first cylindrical wall portion 94 may overlap substantially half the second cylindrical wall portion 95.

A first gap 111 is formed between a first stepped portion 107, which is located on a proximal side of the first cylindrical wall portion 94, and the second edge 95A that is located at the distal end of the second cylindrical wall portion 95. Similarly, a second gap 112 is formed between a second stepped portion 108, which is located on a proximal side of the second cylindrical wall portion 95, and the first edge 94A that is located at the distal end of the first cylindrical wall portion 94. By the first gap 111 and second gap 112, a bending of the annular portion occurring due to external force or the like, that is, a slight movement of the first cylindrical wall portion 94 and second cylindrical wall portion 95 in the circumferential direction R, can be absorbed.

Referring to FIG. 16, FIG. 17, etc., the function of the cover 17 of the present embodiment will be described. The disassembled state of the cover 17, which is illustrated in FIG. 16, is changed to the state illustrated in FIG. 2, etc., by attaching the covering portion 72 to the cover body 71. At this time, the covering portion 72 overlaps the overlapping portion 106 and protects the overlapping portion 106, and the overlapping state between the first cylindrical wall portion 94 and second cylindrical wall portion 95 is not easily released.

Then, as illustrated in FIG. 5, the cover 17 is attached to the distal structure portion 16. At this time, the restriction portion 93 of the cover 17 is engaged with the guide groove 55 of the main body 16A of the distal structure portion 16, and the cover 17 is moved along the longitudinal direction L.

In the endoscope 12, in the state in which the cover 17 is attached to the distal structure portion 16, the insertion section 15 is inserted into a tract such as a lumen cavity, and observation and a proper treatment are performed. In the present embodiment, the overlapping portion 106 is formed by the first cylindrical wall portion 94 and second cylindrical wall portion 95, and the overlapping portion 106 is held by the covering portion 72 from the outside. Thereby, frictional force occurs between the first cylindrical wall portion 94 and second cylindrical wall portion 95. Thus, the second cylindrical wall portion 95 is not easily separated from the first cylindrical wall portion 94. Even if the annular portion 73 bends due to force received from an inner wall of the tract or the like in the body, the bending of the annular portion 73 (a slight movement of the first cylindrical wall portion 94 and second cylindrical wall portion 95 in the circumferential direction R) can be absorbed by the first gap 111 and second gap 112. Thereby, the second cylindrical wall portion 95 is prevented from dropping or lifting from the first cylindrical wall portion 94. It is thus possible to prevent such a problem that the cover 17 drops from the distal structure portion 16 when not intended by the user.

After the use of the endoscope 12, the cover 17 and covering portion 72 are removed from the distal structure portion 16. In the present embodiment, as illustrated in FIG. 16, etc., the annular portion 73 is divided in advance in the dividing portion 74. Thus, in order to remove the cover, the worker does not need to perform such work as breaking a part of the annular portion 73. As illustrated in FIG. 6, if the worker pushes the opening edge portion 86 (right-side edge portion 86A) by the finger F with a relatively weak force in a direction toward the engaging portion 92, the rotation of the cover 17 is restricted by the engagement between the guide groove 55 of the distal structure portion 16 and the restriction portion 93 of the cover body 71. If the worker continues the pushing, the cover body 71 and covering portion 72 elastically deform such that the slit 84 widens (i.e. such that the overlapping state between the first cylindrical wall portion 94 and second cylindrical wall portion 95 is released), and the engagement between the engaging pin 22 and engaging portion 92 is relatively easily released. At this time, since no breakage occurs in the annular portion 73 and dividing portion 74, the worker can perform the work with a relatively weak force.

In the state in which the engagement between the engaging pin 22 and engaging portion 92 is released in this manner, the cover 17 is pulled out to the distal direction L1 side of the longitudinal direction L, and thereby the cover 17 can be removed from the distal structure portion 16. At this time, since the annular portion 73 and dividing portion 74 include no sharp broken part, the worker can safely perform the removing work. The cover 17, which was removed from the distal structure portion 16, is discarded.

The endoscope 12 (distal structure portion 16), from which the cover 17 was removed, is cleaned, disinfected and sterilized. Then, a new cover 17 is properly attached to the distal structure portion 16, and the endoscope system 11 is used for the next-time observation and treatment.

According to the present embodiment, the dividing portion 74 includes the first cylindrical wall portion 94, and the second cylindrical wall portion 95 which is opposed to the first cylindrical wall portion 94, and at least a part of the first cylindrical wall portion 94 overlaps the second cylindrical wall portion 95. According to this configuration, the overlapping portion 106 can be formed by the first cylindrical wall portion 94 and second cylindrical wall portion 95, and the rigidity of the cover body 71 can be increased by the frictional force acting between the first cylindrical wall portion 94 and second cylindrical wall portion 95 in the overlapping portion 106. Thereby, the cover 17, which is not easily deformed by external force, can be realized.

Each of the first cylindrical wall portion 94 and second cylindrical wall portion 95 has a less thickness than the other part of the cover body 71. According to this configuration, it is possible to prevent an increase in thickness in the overlapping portion 106 between the first cylindrical wall portion 94 and second cylindrical wall portion 95, and the endoscope 12 and cover 17, which are compact, can be realized.

Figure 18:
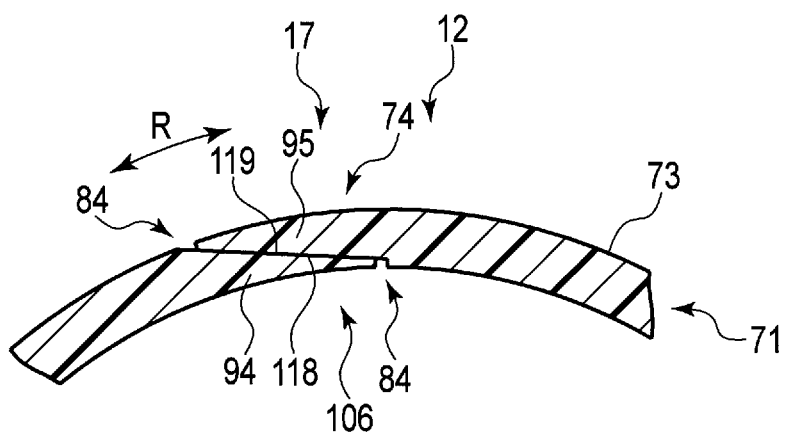
FIG. 18 is a cross-sectional view illustrating a cover body of an endoscope system of an exemplary embodiment, the cover body being cut by a plane crossing the longitudinal direction.

Referring to FIG. 18, a first modification of the endoscope system 11 will be described. The endoscope system 11 of the first modification is different with respect to the shapes of the first cylindrical wall portion 94 and second cylindrical wall portion 95 of the dividing portion 74.

As illustrated in FIG. 18, the slit 84 is continuous with the opening edge portion 86 (proximal-side edge portion 86E) and the proximal edge portion 87, and the slit 84 is formed in a closed shape in the normal state. The dividing portion 74 (slit 84) divides the annular portion 73 in advance, for example, in a direction along the longitudinal direction L, but the direction in which the dividing portion 74 (slit 84) extends is not limited to this direction. The dividing portion 74 includes a first cylindrical wall portion 94 which is located on the side where the engaging portion 92 is provided, and a second cylindrical wall portion 95 which is located on the side where the restriction portion 93 is provided. At least a part of the first cylindrical wall portion 94 overlaps at least a part of the second cylindrical wall portion 95 with respect to the circumferential direction R of the cover 17. The second cylindrical wall portion 95 overlaps the upper side of the first cylindrical wall portion 94. Thus, an overlapping portion 106 is formed in a part where the first cylindrical wall portion 94 and second cylindrical wall portion 95 of the cover body 71 (annular portion 73) overlap.

The first cylindrical wall portion 94 is formed to have a gradually decreasing thickness toward the distal end thereof. The first cylindrical wall portion 94 includes a first inclined surface 118 inclined to the outer peripheral surface of the annular portion 73, and abuts on the second cylindrical wall portion 95 via the first inclined surface 118. The second cylindrical wall portion 95 is formed to have a gradually decreasing thickness toward the distal end thereof. The second cylindrical wall portion 95 includes a second inclined surface 119 inclined to the outer peripheral surface of the annular portion 73, and abuts on the first cylindrical wall portion 94 via the second inclined surface 119. In the present embodiment, although substantially the entirety of the first cylindrical wall portion 94 is configured to overlap the second cylindrical wall portion 95, the mode of the overlapping may be freely set. Needless to say, for example, substantially half the first cylindrical wall portion 94 may overlap substantially half the second cylindrical wall portion 95.

The first inclined surface 118 and second inclined surface 119 can slide on each other in the circumferential direction R. Thus, the bending of the annular portion 73 (a slight movement of the first cylindrical wall portion 94 and second cylindrical wall portion 95 in the circumferential direction R), which occurs due to external force or the like, can be absorbed by the first inclined surface 118 and second inclined surface 119.

According to the endoscope system 11 of the present modification, too, substantially the same advantageous effects can be exhibited.

(Second Modification)

Figure 19:
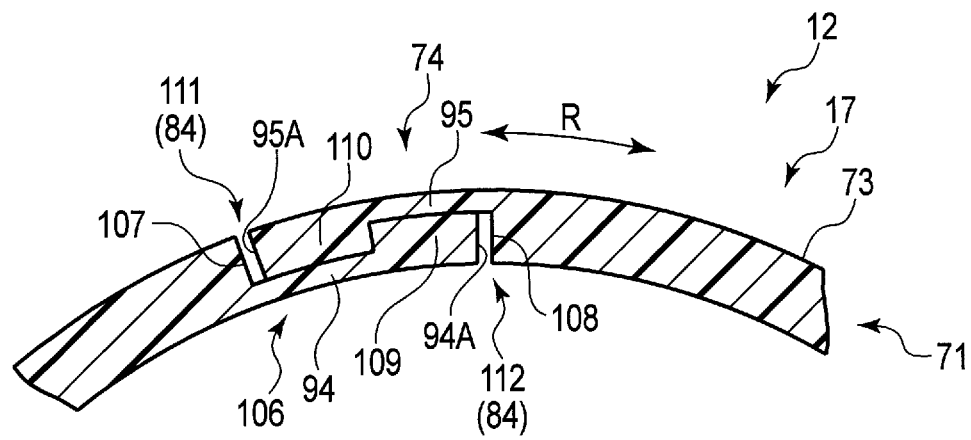
FIG. 19 is a cross-sectional view illustrating a cover body of an endoscope system of an exemplary embodiment, the cover body being cut by a plane crossing the longitudinal direction.

Referring to FIG. 19, a second modification of the endoscope system 11 different with respect to the shapes of the first cylindrical wall portion 94 and second cylindrical wall portion 95 of the dividing portion 74.

As illustrated in FIG. 19, the slit 84 is continuous with the opening edge portion 86 (proximal-side edge portion 86E) and the proximal edge portion 87, and the slit 84 is formed in a closed shape in the normal state. The dividing portion 74 (slit 84) divides the annular portion 73 in advance, for example, in a direction along the longitudinal direction L, but the direction in which the dividing portion 74 (slit 84) extends is not limited to this direction. The dividing portion 74 includes a first cylindrical wall portion 94 which is located on the side where the engaging portion 92 is provided, and a second cylindrical wall portion 95 which is located on the side where the restriction portion 93 is provided. At least a part of the first cylindrical wall portion 94 overlaps at least a part of the second cylindrical wall portion 95 with respect to the circumferential direction R of the cover 17. The second cylindrical wall portion 95 overlaps the upper side of the first cylindrical wall portion 94. Thus, an overlapping portion 106 is formed in a part where the first cylindrical wall portion 94 and second cylindrical wall portion 95 of the cover body 71 (annular portion 73) overlap. In the present embodiment, although substantially the entirety of the first cylindrical wall portion 94 is configured to overlap the second cylindrical wall portion 95, the mode of the overlapping may be freely set. Needless to say, for example, substantially half the first cylindrical wall portion 94 may overlap substantially half the second cylindrical wall portion 95.

The first cylindrical wall portion 94 includes a first engaging portion 109 which is formed of a projection that protrudes toward the second cylindrical wall portion 95 side. The second cylindrical wall portion 95 includes a second engaging portion 110 which is formed of a projection that protrudes toward the first cylindrical wall portion 94 side. The second engaging portion 110 can be engaged with the first engaging portion 109. The first engaging portion 109 is engaged with the second engaging portion 110, and can restrict the movement of the second engaging portion 110 in the circumferential direction R of the annular portion 73. The first engaging portion 109 and second engaging portion 110 are provided in the overlapping portion 106, and are held by the covering portion 72 from the outside. Thus, the engagement state between the first engaging portion 109 and second engaging portion 110 is not easily released.

A first gap 111 is formed between a first stepped portion 107, which is located on a proximal side of the first cylindrical wall portion 94, and the second edge 95A that is located at the distal end of the second cylindrical wall portion 95. Similarly, a second gap 112 is formed between a second stepped portion 108, which is located on a proximal side of the second cylindrical wall portion 95, and the first edge 94A that is located at the distal end of the first cylindrical wall portion 94. The bending of the annular portion 73 (a slight movement of the first cylindrical wall portion 94 and second cylindrical wall portion 95 in the circumferential direction R), which occurs due to external force or the like, can be absorbed by the first gap 111 and second gap 112.

Referring to FIG. 19, etc., the function of the cover 17 of the present modification will be described. The covering portion 72 is attached to the cover body 71, thereby forming the integral cover 17. The covering portion 72 overlaps the overlapping portion 106 and protects the overlapping portion 106.

Then, as illustrated in FIG. 5, the cover 17 is attached to the distal structure portion 16. In the endoscope 12 to which the cover 17 is attached, the insertion section 15 is inserted into a tract such as a lumen cavity, and observation and a proper treatment are performed. In the present modification, in the overlapping portion 106, the first engaging portion 109 of the first cylindrical wall portion 94 and the second engaging portion 110 of the second cylindrical wall portion 95 are engaged. In addition, a part of the overlapping portion 106 (dividing portion 74) is covered and protected by the covering portion 72 from the outside. Thus, the lifting of the second engaging portion 110 is prevented by the covering portion 72, and the engagement state between the first engaging portion 109 and second engaging portion 110 is not easily released. Furthermore, since such a shape is adopted that the projection-shaped first engaging portion 109 and projection-shape second engaging portion 110 are hooked with respect to the circumferential direction R, even if external force is applied in a direction to extend the annular portion 73 in the circumferential direction R, the engagement state between the first engaging portion 109 and second engaging portion 110 is not released. Thus, for example, even if external force is applied in a direction to extend the annular portion 73 while the insertion section 15 is being inserted into the body or the like, the slit 84 does not open. On the other hand, even if external force is applied in a direction to contract the annular portion 73, the bending of the annular portion (a slight movement of the first cylindrical wall portion 94 and second cylindrical wall portion 95 in the circumferential direction R) can be absorbed by the first gap 111 and second gap 112. By these functions, the engagement state between the engaging portion 92 and engaging pin 22 is not released when not intended by the user, and the cover 17 does not drop from the distal structure portion 16.

After the use of the endoscope 12, the cover 17 and covering portion 72 are removed from the distal structure portion 16. In the present embodiment, as illustrated in FIG. 19, the annular portion 73 is divided in advance in the dividing portion 74. Thus, the worker can release the engagement state between the first engaging portion 109 and second engaging portion 110 by applying, by the finger or the like, force to the second cylindrical wall portion 95 in a manner to lift the second cylindrical wall portion 95 (second engaging portion 110) from the first cylindrical wall portion 94 (first engaging portion 109). Further, in the state in which the engagement state is released in this manner, the worker applies force to the opening edge portion 86 (right-side edge portion 86A) by the finger or the like, thereby being able to release the engagement between the engaging portion 92 and engaging pin 22. In this state, by pulling out the cover 17 along the longitudinal direction L, the cover 17 can be removed from the distal structure portion 16. Thereby, the removing work can be performed with a relatively weak force, and the removing work of the cover 17 can be safely performed without forming a broken surface.

According to the present modification, the first cylindrical wall portion 94 includes the first engaging portion 109, and the second cylindrical wall portion 95 includes the second engaging portion 110 which is engaged with the first engaging portion 109. According to this configuration, by the engagement structure which utilizes the first engaging portion 109 and second engaging portion 110, it becomes possible to more surely prevent the slit 84 from opening when not intended by the user.

In this case, the first engaging portion 109 is engaged with the second engaging portion 110 and restricts the movement of the second engaging portion 110 in the circumferential direction R of the annular portion 73. According to this configuration, for example, even if force is applied in a direction to extend the annular portion 73 while the endoscope 12 is being used, it is possible to prevent the overlapping portion 106 from deforming in such a direction as to open the slit 84. Thereby, the cover 17 does not become loose relative to the distal structure portion 16, and it is possible to prevent such a problem that the cover 17 drops from the distal structure portion 16 when not intended by the user.

(Third Modification)

Figure 20:
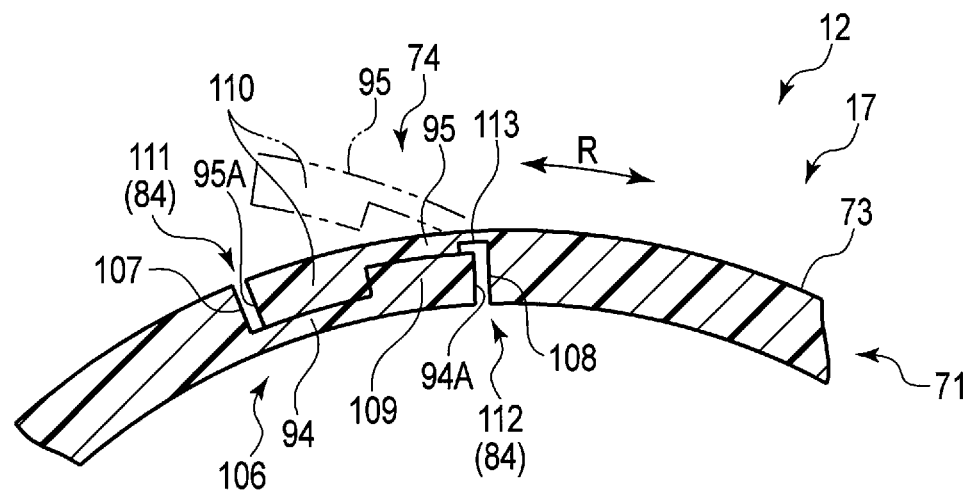
FIG. 20 is a cross-sectional view illustrating a cover body of an endoscope system of an exemplary embodiment, the cover body being cut by a plane crossing the longitudinal direction.

Referring to FIG. 20, a third modification of the endoscope system 11 is different with respect to the shape of the second edge portion 95 of the dividing portion 74.

In the present modification, a fragile portion 113 is provided in a part of the second cylindrical wall portion 95. The fragile portion 113 can deform the second cylindrical wall portion 95 in such a direction as to release the engagement between the first engaging portion 109 and second engaging portion 110. As illustrated in FIG. 20, it is preferable that the fragile portion 113 is provided in the second cylindrical wall portion 95 on a proximal side of the second cylindrical wall portion 95 at a position spaced part from the second engaging portion 110. The fragile portion 113 is formed, for example, as a notch portion which is recessed from a surrounding portion of the second cylindrical wall portion 95. In other words, it can be said that the fragile portion 113 is formed as a thin portion having a less thickness than a surrounding portion of the second cylindrical wall portion 95.

As indicated by a two-dot-and-dash line in FIG. 20, the worker deforms the second cylindrical wall portion 95 by the finger or the like. Thereby, the worker can easily release the engagement state between the first engaging portion 109 and second engaging portion 110. In the present modification, although the fragile portion 113 is provided on the second cylindrical wall portion 95 side, the fragile portion 113 may, needless to say, be provided on the first cylindrical wall portion 94 side, and the first cylindrical wall portion 94 may be configured to be deformable. In this case, it should suffice if a fragile portion 113, which has the same structure as the fragile portion 113 provided in the second cylindrical wall portion 95, is provided in the first cylindrical wall portion 94. In this case, the fragile portion 113 can deform the first cylindrical wall portion 94 in such a direction as to release the engagement between the first engaging portion 109 and second engaging portion 110.

Referring to FIG. 20, the function of the cover 17 of the present modification will be described. When the worker removes the cover 17 from the distal structure portion 16, the worker can release the engagement state between the first engaging portion 109 and second engaging portion 110 by applying, by the finger or the like, force to the second cylindrical wall portion 95 in a manner to lift the second cylindrical wall portion 95 (second engaging portion 110) from the first cylindrical wall portion 94 (first engaging portion 109). At this time, since the fragile portion 113 is provided, the second cylindrical wall portion 95 can easily be deformed with a relatively weak force. Further, in this state, in the same manner as in FIG. 6, the worker applies force to the opening edge portion 86 (right-side edge portion 86A) by the finger F or the like in a direction toward the engaging portion 92, thereby being able to release the engagement between the engaging portion 92 and engaging pin 22. In this state, by pulling out the cover 17 along the longitudinal direction L, the cover 17 can be removed from the distal structure portion 16. Thereby, the removing work can be performed with a relatively weak force, and the removing work of the cover 17 can be safely performed without forming a broken surface.

According to the present modification, one of the first cylindrical wall portion 94 and second cylindrical wall portion 95 is provided with the fragile portion 113 which can deform one of the first cylindrical wall portion 94 and second cylindrical wall portion 95 in such a direction as to release the engagement between the first engaging portion 109 and second engaging portion 110. According to this configuration, since the fragile portion 113 is provided, the engagement between the first engaging portion 109 and second engaging portion 110 can easily be released with a relatively weak force. Thereby, the cover 17 can be removed from the distal structure portion 16 with weak force, and the convenience for the worker can be improved.

Figure 21:
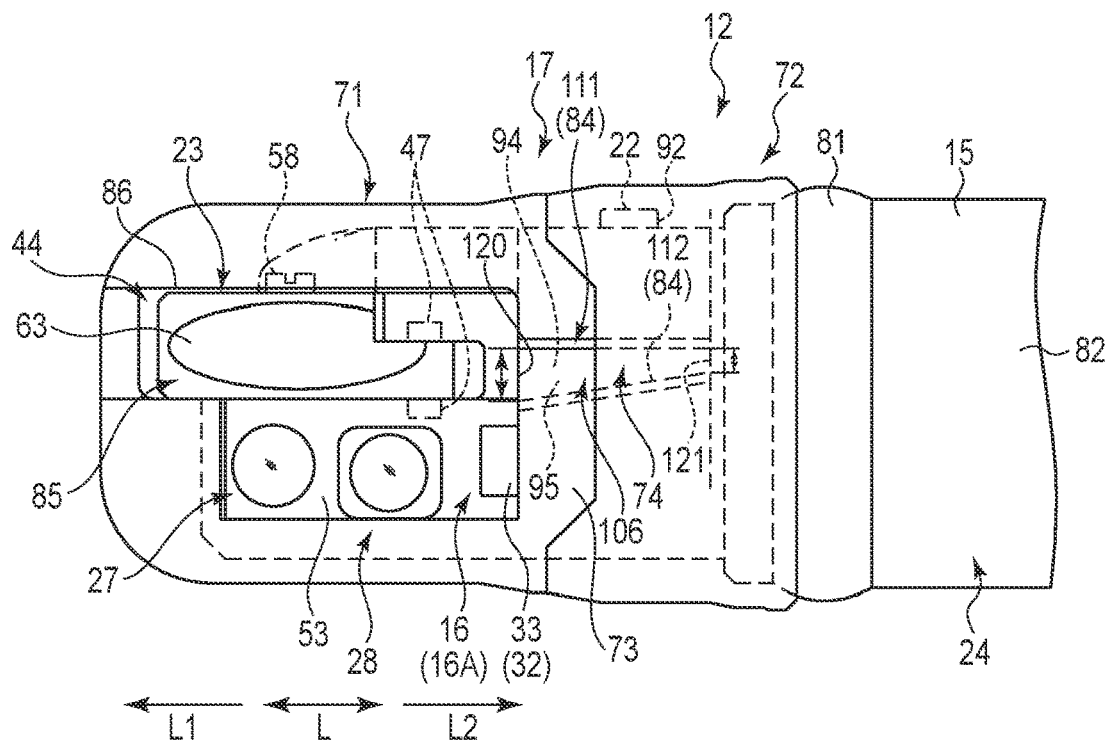
FIG. 21 is a plan view illustrating a distal structure portion of an endoscope system of an exemplary embodiment, and a cover which covers the distal structure portion.

Referring to FIG. 21, a fourth modification of the endoscope system 11 is different with respect to the shapes of the first cylindrical wall portion 94 and second cylindrical wall portion 95 of the dividing portion 74.

The dividing portion 74 includes a first cylindrical wall portion 94 which is located on the side where the engaging portion 92 is provided, and a second cylindrical wall portion 95 which is located on the side where the restriction portion 93 is provided. At least a part of the first cylindrical wall portion 94 overlaps at least a part of the second cylindrical wall portion 95 with respect to the circumferential direction R of the cover 17. The second cylindrical wall portion 95 overlaps the upper side of the first cylindrical wall portion 94. Thus, an overlapping portion 106 is formed in a part where the first cylindrical wall portion 94 and second cylindrical wall portion 95 of the cover body 71 (annular portion 73) overlap. When the cover body 71 is viewed from the outside, the shapes of the first cylindrical wall portion 94 and second cylindrical wall portion 95 are trapezoidal. Each of the first cylindrical wall portion 94 and second cylindrical wall portion 95 is formed to have substantially half the thickness of the other part of the cover body 71. Thus, the cross-sectional shape of the overlapping portion 106 in this modification is substantially similar to the cross-sectional shape illustrated in FIG. 17. In the present embodiment, although substantially the entirety of the first cylindrical wall portion 94 is configured to overlap the second cylindrical wall portion 95, the mode of the overlapping may be freely set. Needless to say, for example, substantially half the first cylindrical wall portion 94 may overlap substantially half the second cylindrical wall portion 95.

In the present modification, the overlapping portion 106 includes a distal overlapping portion 120 which is located on the distal direction L1 side of the longitudinal direction L, and a proximal overlapping portion 121 which is located on the proximal direction L2 side of the longitudinal direction L. With respect to the circumferential direction R of the annular portion 73, the dimension of the distal overlapping portion 120 is greater than the dimension of the proximal overlapping portion 121. Thus, the overlapping portion 106 has an asymmetrical shape with respect to the longitudinal direction L. In addition, even if large external force acts in a direction to open the slit 84 (in the circumferential direction R of the annular portion), the first cylindrical wall portion 94 and second cylindrical wall portion 95 can keep a partially overlapping state in the distal overlapping portion 120 by this asymmetric shape.

A first gap 111 is formed between a first stepped portion 107, which is located on a proximal side of the first cylindrical wall portion 94, and the second edge 95A that is located at the distal end of the second cylindrical wall portion 95. Similarly, a second gap 112 is formed between a second stepped portion 108, which is located on a proximal side of the second cylindrical wall portion 95, and the first edge 94A that is located at the distal end of the first cylindrical wall portion 94. By the first gap 111 and second gap 112, a bending of the annular portion 73 occurring due to external force or the like (a slight movement of the first cylindrical wall portion 94 and second cylindrical wall portion 95 in the circumferential direction R) can be absorbed.

Referring to FIG. 21, etc., the function of the cover 17 of the present embodiment will be described. The covering portion 72 is attached to the cover body 71, thereby forming the integral cover 17. The covering portion 72 overlaps the overlapping portion 106 and protects the overlapping portion 106. Then, as illustrated in FIG. 5, the cover 17 is attached to the distal structure portion 16.

In the endoscope 12 to which the cover 17 is attached, the insertion section is inserted into a tract such as a lumen cavity, and observation and a proper treatment are performed. In the present embodiment, the overlapping portion 106 is formed by the first cylindrical wall portion 94 and the second cylindrical wall portion 95, and is held by the covering portion 72 from the outside. Thereby, frictional force occurs between the first cylindrical wall portion 94 and second cylindrical wall portion 95. Thus, the second cylindrical wall portion 95 is not easily separated from the first cylindrical wall portion 94. Furthermore, even when external force exceeding the frictional force is applied, the first cylindrical wall portion 94 and second cylindrical wall portion 95 can keep a partially overlapping state in the distal overlapping portion 120 by the asymmetric shape. Thus, in this state, the slit 84 does not open. Therefore, additional external force is prevented from acting on the opened slit 84 (dividing portion 74), and it is possible to prevent such a problem that the engagement between the engaging portion 92 and engaging pin 22 is released, with the opened slit 84 (dividing portion 74) being the starting point.

Thus, for example, during the insertion of the insertion section 15 into the body or the like, or during a treatment, even if the cover 17 abuts on an inner wall of the tract or the like in the body, the cover 17 does not drop from the distal structure portion 16. Moreover, even if the annular portion 73 bends due to force received from an inner wall of the tract or the like in the body, the bending of the annular portion 73 (a slight movement of the first cylindrical wall portion 94 and second cylindrical wall portion 95 in the circumferential direction R) can be absorbed by the first gap 111 and second gap 112. Thereby, the second cylindrical wall portion 95 is prevented from lifting from the first cylindrical wall portion 94, and the cover 17 does not drop from the distal structure portion 16 when not intended by the user.

After the use of the endoscope 12, the cover 17 and covering portion 72 are removed from the distal structure portion 16. In the present modification, as illustrated in FIG. 21, etc., the annular portion 73 is divided in advance in the dividing portion 74. Thus, the worker does not need to perform such work as breaking a part of the annular portion 73, in order to remove the cover 17. The worker can easily release the engagement between the engaging pin 22 and engaging portion 92 by pushing the opening edge portion 86 (right-side edge portion 86A) by the finger with a relatively weak force, and by elastically deforming the cover body 71 and covering portion 72 in a manner to widen the slit 84 (in a manner to release the overlapping state between the first cylindrical wall portion 94 and second cylindrical wall portion 95).

In the state in which the engagement between the engaging pin 22 and engaging portion 92 is released in this manner, the worker pulls out the cover 17 to the distal direction L1 side of the longitudinal direction L, and thereby the cover 17 can be removed from the distal structure portion 16. Thereby, the removing work can be performed with a relatively weak force, and the removing work of the cover 17 can be safely performed without forming a broken surface.

According to the present modification, the dividing portion 74 includes the overlapping portion 106 in which the first cylindrical wall portion 94 and second cylindrical wall portion 95 overlap. The overlapping portion 106 includes the distal overlapping portion 120 which is located on the distal direction L1 side of the longitudinal direction L, and the proximal overlapping portion 121 which is located on the proximal direction L2 side of the longitudinal direction L. The dimension of the distal overlapping portion 120 in the circumferential direction R of the annular portion 73 is greater than the dimension of the proximal overlapping portion 121 in the circumferential direction R of the annular portion 73. According to this configuration, the slit 84 does not easily open, even when large force is applied in such a direction as to open the slit 84. Thereby, it is possible to further reduce the possibility of the occurrence of such a problem that the external force further acts, with the slit 84 being the start point, and the cover 17 drops from the distal structure portion 16 when not intended by the user.

(Fifth Modification)

Figure 22:
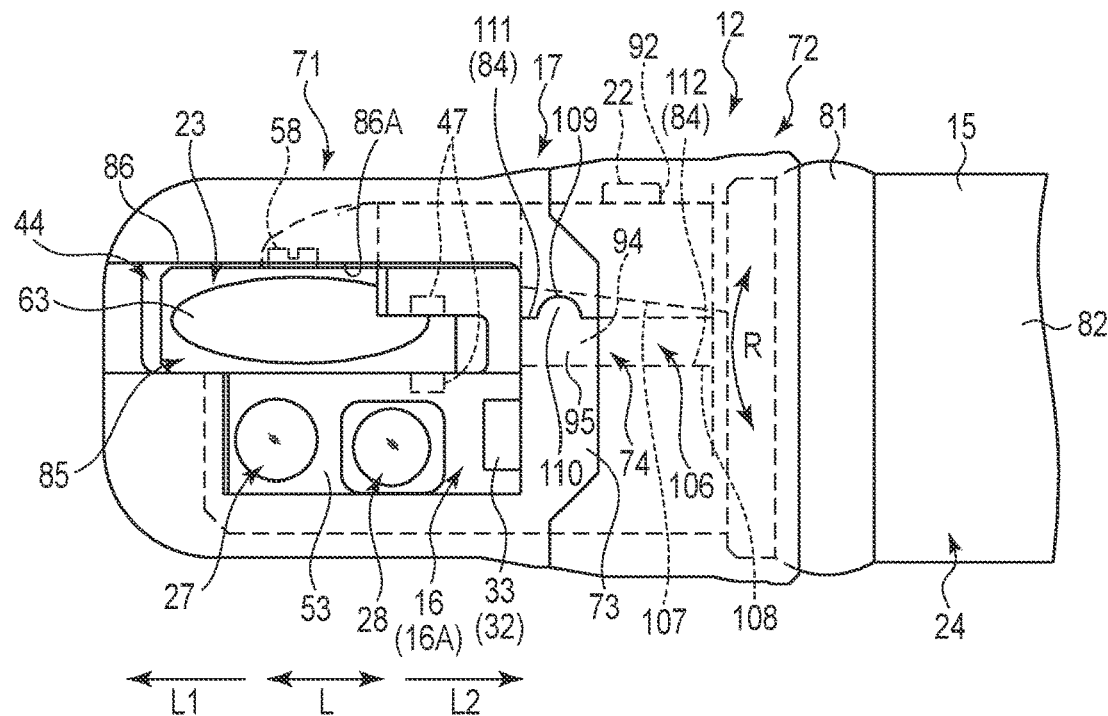
FIG. 22 is a plan view illustrating a distal structure portion of an endoscope system of an exemplary embodiment, and a cover which covers the distal structure portion.
Figure 23:
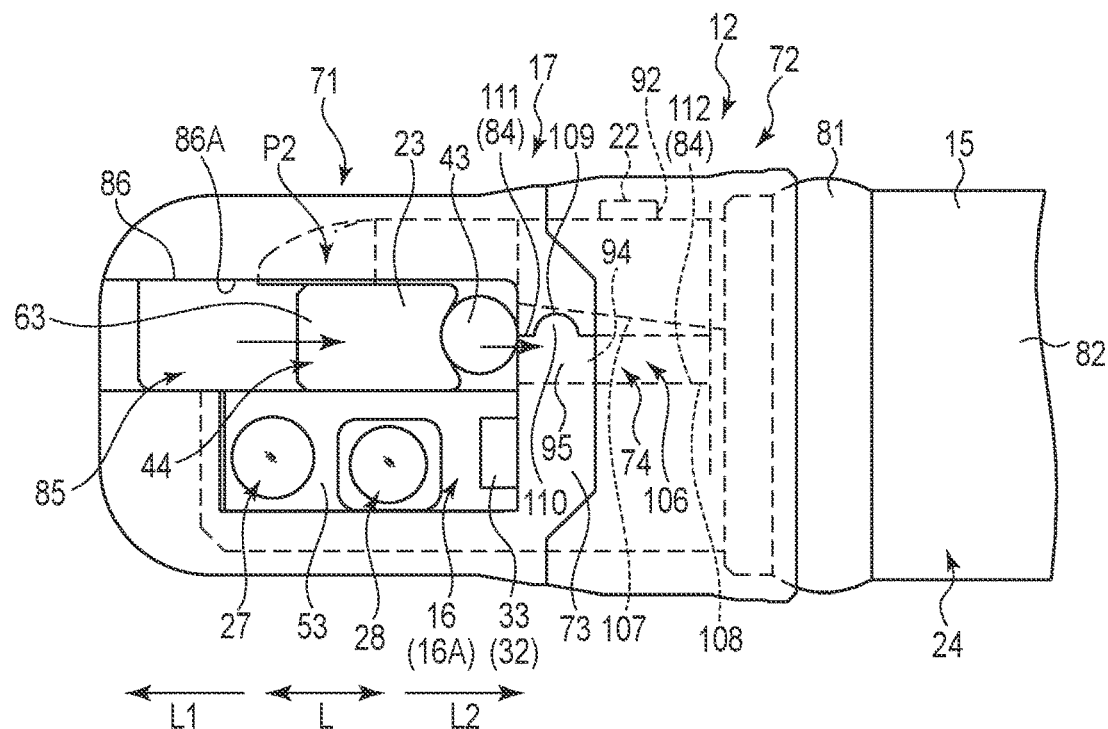
FIG. 23 is a plan view illustrating a state in which a treatment instrument is raised by a pivot mechanism in the endoscope system illustrated in FIG. 22 in a direction passing through the drawing sheet of FIG. 23.

Referring to FIG. 22 and FIG. 23, a fifth modification of the endoscope system 11 is different with respect to the shapes of the first cylindrical wall portion 94 and second cylindrical wall portion 95 of the dividing portion 74.

The dividing portion 74 includes a first cylindrical wall portion 94 which is located on the side where the engaging portion 92 is provided; a first stepped portion 107 which is located on a proximal side of the first cylindrical wall portion 94; a second cylindrical wall portion 95 which is located on the side where the restriction portion 93 is provided; and a second stepped portion 108 which is located on a proximal side of the second cylindrical wall portion 95. At least a part of the first cylindrical wall portion 94 overlaps at least a part of the second cylindrical wall portion 95 with respect to the circumferential direction R of the cover 17. The second cylindrical wall portion 95 overlaps the upper side of the first cylindrical wall portion 94. Thus, an overlapping portion 106 is formed in a part where the first cylindrical wall portion 94 and second cylindrical wall portion 95 of the cover body 71 (annular portion 73) overlap.

The first cylindrical wall portion 94 includes a first engaging portion 109. The first engaging portion 109 has a recess shape which is circularly recessed toward the first stepped portion 107 side. In other words, it can be said that the first engaging portion 109 is circularly recessed in the circumferential direction R of the cover 17. The second cylindrical wall portion 95 includes a second engaging portion 110. The second engaging portion 110 has a projection shape which circularly projects toward the first stepped portion 107 side. In other words, it can be said that the second engaging portion 110 circularly projects in the circumferential direction R of the cover 17. The second engaging portion 110 can be engaged with the first engaging portion 109. In this engagement state, the first engaging portion 109 can restrict the movement of the second engaging portion 110 in the longitudinal direction L.

When the cover body 71 is viewed from the outside, the shapes of the first cylindrical wall portion 94 and second cylindrical wall portion 95 are substantially rectangular. Each of the first cylindrical wall portion 94 and second cylindrical wall portion 95 is formed to have substantially half the thickness of the other part of the cover body 71. In the present embodiment, although substantially the entirety of the first cylindrical wall portion 94 is configured to overlap the second cylindrical wall portion 95, the mode of the overlapping may be freely set. Needless to say, for example, substantially half the first cylindrical wall portion 94 may overlap substantially half the second cylindrical wall portion 95.

A first gap 111 may be formed between the first stepped portion 107 and the second edge 95A which is located at the distal end of the second cylindrical wall portion 95. Similarly, a second gap 112 may be formed between the second stepped portion 108 and the first edge 94A which is located at the distal end of the first cylindrical wall portion 94. By providing the first gap 111 and second gap 112, the bending of the annular portion 73 (a slight movement of the first cylindrical wall portion 94 and second cylindrical wall portion 95 in the circumferential direction R), which occurs due to external force or the like, can be absorbed.

Referring to FIG. 22, FIG. 23, etc., the function of the cover 17 of the present embodiment will be described. The disassembled state of the cover 17 is changed to the state illustrated in FIG. 22, etc., by attaching the covering portion 72 to the cover body 71. At this time, the covering portion 72 overlaps the overlapping portion 106 and protects the overlapping portion 106, and the overlapping state between the first cylindrical wall portion 94 and second cylindrical wall portion 95 is not easily released. Then, as illustrated in FIG. 22, the cover 17 is attached to the distal structure portion 16.

In the endoscope 12, in the state in which the cover 17 is attached to the distal structure portion 16, the insertion section 15 is inserted into a tract such as a lumen cavity, and observation and a proper treatment are performed. In the present modification, the overlapping portion 106 is formed by the first cylindrical wall portion 94 and second cylindrical wall portion 95, and the overlapping portion 106 is held by the covering portion 72 from the outside. Thereby, frictional force occurs between the first cylindrical wall portion 94 and second cylindrical wall portion 95. Further, since the second engaging portion 110 is engaged with the first engaging portion 109, the second cylindrical wall portion 95 is not displaced from the first cylindrical wall portion 94 in the longitudinal direction L. In the meantime, as illustrated in FIG. 23, when the direction-changing mechanism 44 (pivot base 23) is rotated and the treatment instrument 43 is raised in the direction passing through the drawing sheet of FIG. 23, there is a case where an urging force of the direction-changing mechanism 44 is transmitted to the annular portion 73 via the treatment instrument 43. Even in such a case, the first engaging portion 109 and second engaging portion 110 are engaged, and the second cylindrical wall portion 95 is not displaced from the first cylindrical wall portion 94 in the longitudinal direction L. In this manner, in the present modification, even when some external force acts on the cover 17, the second cylindrical wall portion 95 is not easily separated from the first cylindrical wall portion 94.

Thus, for example, during the insertion of the insertion section 15 into the body or the like, or during a treatment, even if the cover 17 abuts on an inner wall of the tract or the like in the body, the cover 17 does not drop from the distal structure portion 16. Moreover, in the case where the first gap 111 and second gap 112 are provided, even if bending occurs in the annular portion 73 (a slight movement of the first cylindrical wall portion 94 and second cylindrical wall portion 95 in the circumferential direction R) due to force received from an inner wall of the tract or the like in the body, the bending of the annular portion 73 can be absorbed by the first gap 111 and second gap 112. Thereby, the second cylindrical wall portion 95 does not drop from the first cylindrical wall portion 94, and the cover 17 does not drop from the distal structure portion 16 when not intended by the user.

After the use of the endoscope 12, the cover 17 and covering portion 72 are removed from the distal structure portion 16. The worker can easily release the engagement between the engaging pin 22 and engaging portion 92 by pushing the opening edge portion 86 (right-side edge portion 86A) by the finger with a relatively weak force, and by elastically deforming the cover body 71 and covering portion 72 in a manner to widen the slit 84 (in a manner to release the overlapping state between the first cylindrical wall portion 94 and second cylindrical wall portion 95).

In the state in which the engagement between the engaging pin 22 and engaging portion 92 is released in this manner, the cover 17 is pulled out to the distal direction L1 side of the longitudinal direction L, and thereby the cover 17 can be removed from the distal structure portion 16. Thereby, the removing work can be performed with a relatively weak force, and the removing work of the cover 17 can be safely performed without forming a broken surface.

According to the present modification, the first engaging portion 109 is engaged with the second engaging portion 110, and restricts the movement of the second engaging portion 110 in the longitudinal direction L. According to this configuration, when external force is applied to the cover 17, it is possible to prevent the position of the second cylindrical wall portion 95 from being displaced from the first cylindrical wall portion 94 in the longitudinal direction L. Thereby, it is possible to maintain the configuration in which the first cylindrical wall portion 94 and second cylindrical wall portion 95 exhibit mutual frictional force, while keeping the state in which the second cylindrical wall portion 95 overlaps the first cylindrical wall portion 94. Thereby, it is possible to further reduce the possibility of the occurrence of such a problem that the cover 17 drops from the distal structure portion 16 when not intended by the user.

(Sixth Modification)

Figure 24:
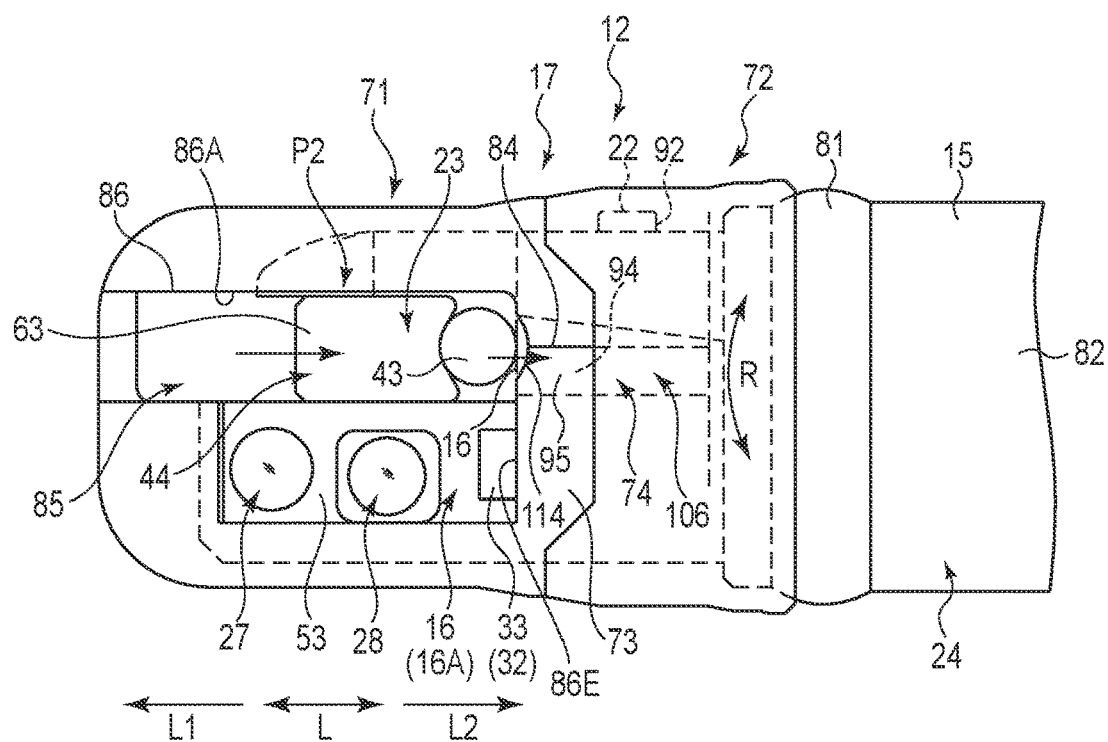
FIG. 24 is a plan view illustrating a distal structure portion of an endoscope system of an exemplary embodiment, and a cover which covers the distal structure portion.

Referring to FIG. 24, a sixth modification of the endoscope system 11 is different with respect to the shape of the proximal-side edge portion 86E of the opening edge portion 86.

The proximal-side edge portion 86E includes a recess portion 114 at a position neighboring the dividing portion 74. The recess portion 114 is circularly recessed toward the proximal direction side L2 in the longitudinal direction L. In other words, it can be said that the recess portion 114 has an arcuate shape which matches with the circular cross-sectional shape of the treatment instrument 43. The recess portion 114 exposes the rigid distal structure portion 16 which is located inside the recess portion 114. Thus, the recess portion 114 is located on the proximal direction L2 side with respect to one of the surfaces of the distal structure portion 16. The dividing portion 74 and slit 84 are formed in a manner to correspond to a bottom portion of the recess portion 114.

A first gap 111 may be formed between the first stepped portion 107 which is located on the proximal side of the first cylindrical wall portion 94, and the second edge 95A which is located at the distal end of the second cylindrical wall portion 95. Similarly, a second gap 112 may be formed between the second stepped portion 108 which is located on the proximal side of the second cylindrical wall portion 95, and the first edge 94A which is located at the distal end of the first cylindrical wall portion 94. By the first gap 111 and second gap 112, the bending of the annular portion (a slight movement of the first cylindrical wall portion 94 and second cylindrical wall portion 95 in the circumferential direction R), which occurs due to external force or the like, can be absorbed.

Referring to FIG. 24, etc., the function of the cover 17 of the present embodiment will be described. The disassembled state of the cover 17 is changed to the state illustrated in FIG. 24, etc., by attaching the covering portion 72 to the cover body 71. At this time, the covering portion 72 overlaps the overlapping portion 106 and protects the overlapping portion 106, and the overlapping state between the first cylindrical wall portion 94 and second cylindrical wall portion 95 is not easily released. Then, as illustrated in FIG. 24, the cover 17 is attached to the distal structure portion 16.

In the endoscope 12, in the state in which the cover 17 is attached to the distal structure portion 16, the insertion section 15 is inserted into a tract such as a lumen cavity, and observation and a proper treatment are performed. In the present modification, the overlapping portion 106 is formed by the first cylindrical wall portion 94 and second cylindrical wall portion 95, and the overlapping portion 106 is held by the covering portion 72 from the outside. Thereby, frictional force occurs between the first cylindrical wall portion 94 and second cylindrical wall portion 95. Thus, in the present modification, even when some external force acts on the cover 17, the second cylindrical wall portion is not easily separated from the first cylindrical wall portion 94.

In the meantime, as illustrated in FIG. 24, when the direction-changing mechanism 44 (pivot base 23) is rotated and the treatment instrument 43 is raised in the direction passing through the drawing sheet of FIG. 24, there is a case where an urging force of the direction-changing mechanism 44 is transmitted to the annular portion 73 via the treatment instrument 43. Even in such a case, in the present modification, since the proximal-side edge portion 86E is provided with the recess portion 114, the urging force is not transmitted to the annular portion 73. This urging force is transmitted to only the rigid distal structure portion 16. Thus, no deformation occurs in the annular portion 73 and dividing portion 74 due to the urging force. In addition, even when external force due to a cause other than the direction-changing mechanism 44 acts on the vicinity of the proximal-side edge portion 86E, a structure around the proximal-side edge portion 86E is configured to be evacuated by the recess portion 114. Thus, the external force does not easily act on the vicinity of the proximal-side edge portion 86E.

Thus, for example, during the insertion of the insertion section 15 into the body or the like, or during a treatment, even if the cover 17 abuts on an inner wall of the tract or the like in the body, the cover 17 does not drop from the distal structure portion 16. Moreover, in the case where the first gap 111 and second gap 112 are provided, even if bending occurs in the annular portion 73 due to force received from an inner wall of the tract or the like in the body, the bending of the annular portion 73 can be absorbed by the first gap 111 and second gap 112. Thereby, the second cylindrical wall portion 95 is prevented from dropping from the first cylindrical wall portion 94, and it is possible to further reduce the possibility of the occurrence of such a problem that the cover 17 drops from the distal structure portion 16 when not intended by the user.

After the use of the endoscope 12, the cover 17 and covering portion 72 are removed from the distal structure portion 16. The worker can easily release the engagement between the engaging pin 22 and engaging portion 92 by pushing the opening edge portion 86 (right-side edge portion) by the finger with a relatively weak force, and by elastically deforming the cover body 71 and covering portion 72 in a manner to widen the slit 84 (in a manner to release the overlapping state between the first cylindrical wall portion 94 and second cylindrical wall portion 95).

In the state in which the engagement between the engaging pin 22 and engaging portion 92 is released in this manner, the cover 17 is pulled out to the distal direction L1 side of the longitudinal direction L, and thereby the cover 17 can be removed from the distal structure portion 16. Thereby, the removing work can be performed with a relatively weak force, and the removing work of the cover 17 can be safely performed without forming a broken surface.

The opening edge portion 86 includes the proximal-side edge portion 86E provided at a position neighboring the dividing portion 74, and the proximal-side edge portion 86E forms the recess portion 114 which is recessed toward the proximal side in the longitudinal direction L. According to this configuration, external force acts less easily on the proximal-side edge portion 86E by virtue of the structure. It is thus possible to reduce the possibility that deformation by external force occurs in the neighboring dividing portion 74. Thereby, it is possible to further reduce the possibility of the occurrence of such a problem that the cover 17 drops from the distal structure portion 16 when not intended by the user.

(Seventh Modification)

Referring to FIG. 25 and FIG. 26, a seventh modification of the endoscope system 11 is different with respect to the shape of the dividing portion 74 and the shape of the covering portion 72.

The cover 17 includes a cover body 71 and a covering portion 72. The dividing portion 74 includes a first cylindrical wall portion 94 which is located on the side where the engaging portion 92 is provided, and a second cylindrical wall portion 95 which is located on the side where the restriction portion 93 is provided. At least a part of the first cylindrical wall portion 94 overlaps at least a part of the second cylindrical wall portion 95 with respect to the circumferential direction R of the cover 17. When the cover body 71 is viewed from the outside, the first cylindrical wall portion 94 and second cylindrical wall portion 95 have substantially rectangular shapes. The second cylindrical wall portion 95 overlaps the upper side of the first cylindrical wall portion 94. Thus, an overlapping portion 106 is formed in a part where the first cylindrical wall portion 94 and second cylindrical wall portion 95 of the cover body 71 (annular portion 73) overlap. The first cylindrical wall portion 94 includes a first through-hole 115. The first through-hole 115 has, for example, a circular shape. The second cylindrical wall portion 95 includes a second through-hole 116 in a position overlapping the first through-hole 115. The second through-hole 116 has, for example, a circular shape.

Each of the first cylindrical wall portion 94 and second cylindrical wall portion 95 is formed to have substantially half the thickness of the other part of the cover body 71. In the present embodiment, although substantially the entirety of the first cylindrical wall portion 94 is configured to overlap the second cylindrical wall portion 95, the mode of the overlapping may be freely set. Needless to say, for example, substantially half the first cylindrical wall portion 94 may overlap substantially half the second cylindrical wall portion 95.

A first gap 111 is formed between a first stepped portion 107, which is located on a proximal side of the first cylindrical wall portion 94, and the second edge 95A that is located at the distal end of the second cylindrical wall portion 95. Similarly, a second gap 112 is formed between a second stepped portion 108, which is located on a proximal side of the second cylindrical wall portion 95, and the first edge 94A that is located at the distal end of the first cylindrical wall portion 94. By the first gap 111 and second gap 112, a bending of the annular portion occurring due to external force or the like (a slight movement of the first cylindrical wall portion 94 and second cylindrical wall portion 95 in the circumferential direction R) can be absorbed.

The covering portion 72 is formed of, for example, a material (synthetic rubber or the like) having rubber-like elasticity, in a cylindrical or annular shape. As illustrated in FIG. 3 and FIG. 4, the covering portion 72 includes, on its inner peripheral surface, an annular projection portion 76 which is engaged in the engaging portion 75 of the cover body 71; an annular engaging recess portion 77 in which the flange portion 88 is engaged; and an engaging projection portion 117 (penetration portion) provided on the annular projection portion 76 so as to be engaged in the inside of the first through-hole 115 and second through-hole 116. Thus, as illustrated in FIG. 25, when the covering portion 72 is attached to the annular portion 73 of the cover body 71, the annular projection portion 76 of the covering portion 72 is engaged with the engaging portion 75 of the cover body 71, the engaging recess portion 77 of the covering portion 72 is engaged with the flange portion 88 of the cover body 71, and the engaging projection portion 117 (penetration portion) of the covering portion is engaged in the first through-hole 115 and second through-hole 116 of the cover body 71. Thereby, the engaging projection portion 117 (penetration portion)

can be engaged with the first cylindrical wall portion 94 and second cylindrical wall portion 95. In the present modification, in this manner, since the engaging projection portion 117 is passed through the inside of the first through-hole 115 and second through-hole 116, it is possible to prevent the position of the second cylindrical wall portion 95 from being displaced from the first cylindrical wall portion 94.

Referring to FIG. 25, FIG. 26, etc., the function of the cover 17 of the present embodiment will be described. From the disassembled state of the cover 17, the covering portion 72 is attached to the cover body 71 (FIG. 25 illustrates the state in which the covering portion 72 is attached to the cover body 71). At this time, the covering portion 72 overlaps the overlapping portion 106 and protects the overlapping portion 106, and the overlapping state between the first cylindrical wall portion 94 and second cylindrical wall portion 95 is not easily released. Then, the cover 17 is attached to the distal structure portion 16, as in the state illustrated in FIG. 25.

In the endoscope 12, in the state in which the cover 17 is attached to the distal structure portion 16, the insertion section 15 is inserted into a tract such as a lumen cavity, and observation and a proper treatment are performed. In the present modification, the overlapping portion 106 is formed by the first cylindrical wall portion 94 and second cylindrical wall portion 95, and the overlapping portion 106 is held by the covering portion 72 from the outside. Thereby, frictional force occurs between the first cylindrical wall portion 94 and second cylindrical wall portion 95. Further, since the engaging projection portion 117 is engaged in the inside of the first through-hole 115 and second through-hole 116, the second cylindrical wall portion 95 is not displaced from the first cylindrical wall portion 94 in this engagement state. Thus, the second cylindrical wall portion 95 is not easily separated from the first cylindrical wall portion 94. Therefore, for example, during the insertion of the insertion section 15 into the body or the like, or during a treatment, even if the cover 17 abuts on an inner wall of the tract or the like in the body, there occurs no such problem that the cover 17 drops from the distal structure portion 16. Moreover, even if the annular portion 73 bends due to force received from an inner wall of the tract or the like in the body, the bending of the annular portion 73 can be absorbed by the first gap 111 and second gap 112. Thereby, the second cylindrical wall portion 95 is prevented from lifting from the first cylindrical wall portion 94, and such a problem does not occur that the cover 17 drops from the distal structure portion 16 when not intended by the user.

After the use of the endoscope 12, the cover 17 and covering portion 72 are removed from the distal structure portion 16. In the present embodiment, as illustrated in FIG. 25, etc., the annular portion 73 is divided in advance in the dividing portion 74. Thus, in order to remove the cover 17, the worker does not need to perform such work as breaking a part of the annular portion 73. Before removing the cover 17, the worker first rotates the covering portion 72 by the finger or the like by a small angle around the center axis C, or moving the position of the covering portion 72 by a small distance in the longitudinal direction L, thereby releasing the engagement state of the engaging projection portion 117 in the first through-hole 115 and second through-hole 116. Thereby, the second cylindrical wall portion 95 becomes movable relative to the first cylindrical wall portion 94.

In this state, in the same manner as illustrated in FIG. 6, the worker pushes the opening edge portion 86 (right-side edge portion 86A) by the finger F with a relatively weak force, and elastically deforms the cover body 71 and covering portion 72 such that the slit 84 becomes wider (i.e. such that the engagement state between the first cylindrical wall portion 94 and second cylindrical wall portion 95 is released). Thereby, the engagement between the engaging pin 22 and engaging portion 92 can relatively easily released. Thus, the worker can perform the work with a relatively weak force, and no load is imposed on the worker.

In the state in which the engagement between the engaging pin 22 and engaging portion 92 is released in this manner, the cover 17 is pulled out to the distal direction L1 side of the longitudinal direction L, and thereby the cover 17 can be removed from the distal structure portion 16. Thereby, the removing work can be performed with a relatively weak force, and the removing work of the cover 17 can be safely performed without forming a broken surface.

According to the present modification, the dividing portion 74 includes the overlapping portion 106 in which the first cylindrical wall portion 94 and second cylindrical wall portion 95 overlap, and the covering portion 72 includes the penetration portion which penetrates the overlapping portion 106 and is engaged with the first cylindrical wall portion 94 and second cylindrical wall portion 95. According to this configuration, by the simple structure using the penetration portion, the shape of the overlapping portion 106, in which the first cylindrical wall portion 94 and second cylindrical wall portion 95 overlap, can be maintained. Thus, it is possible to further reduce the possibility of the occurrence of such a problem that the cover 17 drops from the distal structure portion 16 when not intended by the user.

In the above-described embodiments and modifications, the example in which the distal structure portion 16 is of a side-viewing type was described. However, needless to say, the distal structure portion 16 may be formed as a so-called forward-viewing type for observation in a direction along the longitudinal direction L of the insertion section 15, or may be formed as an oblique-viewing type for observation in an arbitrary direction in a range between the direction along the longitudinal axis L of the insertion section and the direction perpendicular to the longitudinal axis L.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cover attached to a distal structure portion of an insertion section of an endoscope, the cover comprising:
   a cover body including:
   an opening edge portion that defines a surrounding of an opening that exposes a part of the distal structure portion,
   an annular portion that surrounds a periphery of the distal structure portion,
   a proximal edge portion that is provided on the annular portion and is located at a proximal end in a longitudinal direction of the insertion section,
   a dividing portion that is provided in the annular portion and defines a slit and provides a continuous passage between the opening edge portion and the proximal edge portion, the dividing portion including:
   a first cylindrical wall portion that defines a first edge of the annular portion;

a second cylindrical wall portion that defines a second edge of the annular portion; and
an overlapping portion wherein the first cylindrical wall portion and the second cylindrical wall portion overlap; and
a covering portion configured to cover a part of the annular portion where at least the overlapping portion of the dividing portion is provided.

2. The cover of claim 1, wherein the covering portion is configured to annularly cover the annular portion.

3. The cover of claim 1, wherein the covering portion has elasticity and is put in close contact with an outer periphery of the annular portion.

4. The cover of claim 1, wherein each of the first cylindrical wall portion and the second cylindrical wall portion has a smaller thickness than other parts of the cover body.

5. The cover of claim 1, wherein:
the overlapping portion includes:
a distal overlapping portion; and
a proximal overlapping portion, the distal overlapping portion located distally of the proximal overlapping portion; and
a dimension of the distal overlapping portion along a circumferential direction of the annular portion is greater than a dimension of the proximal overlapping portion along the circumferential direction of the annular portion.

6. The cover of claim 1, wherein the covering portion includes a penetration portion configured to penetrate the overlapping portion and engage with the first cylindrical wall portion and the second cylindrical wall portion.

7. The cover of claim 1, wherein:
the first cylindrical wall portion includes a first engaging portion, and
the second cylindrical wall portion includes a second engaging portion engaged with the first engaging portion.

8. The cover of claim 7, wherein the first engaging portion is engaged with the second engaging portion and restricts movement of the second engaging portion in the longitudinal direction.

9. The cover of claim 7, wherein the first engaging portion is engaged with the second engaging portion and restricts a movement of the second engaging portion in a circumferential direction of the annular portion.

10. The cover of claim 9, wherein one of the first cylindrical wall portion and the second cylindrical wall portion is provided with a fragile portion configured to deform one of the first cylindrical wall portion and the second cylindrical wall portion to release engagement between the first engaging portion and the second engaging portion.

11. The cover of claim 1, wherein:
the cover body includes, in a vicinity of the dividing portion, an engaging portion which is engaged with the distal structure portion, and
engagement between the engaging portion and the distal structure portion is released when the slit is opened.

12. The cover of claim 11, wherein:
the cover body includes a restriction portion on an opposite side of the engaging portion with the dividing portion being interposed such that the restriction portion is provided distally of the engagement portion; and
the restriction portion is configured engage with the distal structure portion and to restrict rotation of the cover body relative to the distal structure portion.

13. The cover of claim 1, wherein:
the opening edge portion includes a proximal-side edge portion provided adjacent to the dividing portion, and
the proximal-side edge portion forms a recess portion that is recessed toward a proximal side in the longitudinal direction.

14. The cover of claim 1, wherein the dividing portion further includes a first stepped portion on a proximal side of the first cylindrical wall portion and a second stepped portion on a proximal side of the second cylindrical wall portion.

15. The cover of claim 1, wherein the first cylindrical wall portion and the second cylindrical wall portion form a trapezoidal shape when viewed from outside the cover body.

16. An endoscope system comprising:
the cover of claim 1; and
the endoscope including the insertion section with the distal structure portion at a distal side of the insertion section, wherein:
the cover is attached to an outside of the distal structure portion.

17. The endoscope system of claim 16, wherein:
the distal structure portion of the endoscope includes a treatment instrument raising base configured to change a direction of a distal side of a treatment instrument which is passed through the insertion section, and
the opening edge portion is configured to expose the treatment instrument raising base.

* * * * *